(12) United States Patent
Ryan et al.

(10) Patent No.: US 9,283,073 B2
(45) Date of Patent: Mar. 15, 2016

(54) ANNULOPLASTY RING AND METHOD

(75) Inventors: Timothy R. Ryan, Shorewood, MN (US); Cathleen A. Bergin, Hugo, MN (US); Jerald Redmond, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 1565 days.

(21) Appl. No.: 11/809,194

(22) Filed: May 31, 2007

(65) Prior Publication Data

US 2007/0299513 A1    Dec. 27, 2007

Related U.S. Application Data

(60) Provisional application No. 60/810,600, filed on Jun. 2, 2006.

(51) Int. Cl.
*A61F 2/24* (2006.01)

(52) U.S. Cl.
CPC ............. *A61F 2/2448* (2013.01); *A61F 2/2466* (2013.01); *A61F 2/2496* (2013.01); *A61F 2250/0018* (2013.01); *A61F 2250/0029* (2013.01)

(58) Field of Classification Search
CPC .... A61F 2/2445; A61F 2/2448; A61F 2/2451
USPC .......................................... 623/2, 2.36, 2.11
See application file for complete search history.

(56) References Cited

U.S. PATENT DOCUMENTS

| | | |
|---|---|---|
| 3,656,185 A | 4/1972 | Carpentier |
| 3,966,401 A | 6/1976 | Hancock et al. |
| 4,050,893 A | 9/1977 | Hancock et al. |
| 4,055,861 A | 11/1977 | Carpentier et al. |

(Continued)

FOREIGN PATENT DOCUMENTS

| | | |
|---|---|---|
| EP | 0 257 874 | 6/1987 |
| EP | 0 338 994 | 10/1989 |

(Continued)

OTHER PUBLICATIONS

Lawrence et al., "A Biomechanical Analysis of Suture Materials and Their Influence on a Four-Strand Flexor Tendon Repair," The Journal of Hand Surgery, W.B. Saunders, vol. 30, No. 4, Jul. 2005, pp. 836-841.

(Continued)

*Primary Examiner* — Thomas J Sweet
*Assistant Examiner* — Seema Mathew

(57) ABSTRACT

An annuloplasty ring including a sheath, an arcuate stiffening element, and a tensioning member. The stiffening element is disposed within the sheath and defines discrete, first and second ends separated by a lateral spacing. The tensioning member extends between the stiffening element ends. The tensioning member is characterized as being more flexible than the stiffening element and is configured to provide a taut state in which the tensioning member is substantially non-extensible and impedes expansion of the lateral spacing. With this configuration, the stiffening element serves to remodel the valve annulus to a desired shape, while the tensioning member exhibits sufficient flexibility to allow for natural movement of the valve annulus while limiting (in the taut state) the extent of annular dilatation (e.g., overt lateral separation of the first and second ends of the stiffening member) due to in vivo forces.

26 Claims, 10 Drawing Sheets

(56) References Cited

U.S. PATENT DOCUMENTS

| | | | |
|---|---|---|---|
| 4,164,046 A | 8/1979 | Cooley | |
| 4,182,446 A | 1/1980 | Penny | |
| 4,917,698 A | 4/1990 | Carpentier et al. | |
| 5,011,481 A | 4/1991 | Myers et al. | |
| 5,041,130 A | 8/1991 | Cosgrove et al. | |
| 5,061,277 A | 10/1991 | Carpentier et al. | |
| 5,104,407 A | 4/1992 | Lam et al. | |
| 5,201,880 A | 4/1993 | Wright et al. | |
| 5,258,021 A | 11/1993 | Duran | |
| 5,306,296 A | 4/1994 | Wright et al. | |
| 5,350,420 A | 9/1994 | Cosgrove et al. | |
| 5,376,112 A | 12/1994 | Duran | |
| 5,496,336 A | 3/1996 | Cosgrove et al. | |
| 5,522,884 A | 6/1996 | Wright | |
| 5,593,424 A | 1/1997 | Northrup, III | |
| 5,601,576 A | 2/1997 | Garrison | |
| 5,607,471 A | 3/1997 | Seguin et al. | |
| 5,617,397 A | 4/1997 | Jones et al. | |
| 5,669,919 A | 9/1997 | Sanders et al. | |
| 5,674,279 A | 10/1997 | Wright et al. | |
| 5,674,280 A | 10/1997 | Davidson et al. | |
| 5,683,402 A | 11/1997 | Cosgrove et al. | |
| 5,716,397 A | 2/1998 | Myers | |
| 5,824,066 A | 10/1998 | Gross | |
| 5,860,992 A | 1/1999 | Daniel et al. | |
| 5,972,030 A | 10/1999 | Garrison et al. | |
| 6,102,945 A | 8/2000 | Campbell | |
| 6,143,024 A * | 11/2000 | Campbell et al. | 623/2.36 |
| 6,159,240 A | 12/2000 | Sparer et al. | |
| 6,165,183 A | 12/2000 | Kuehn et al. | |
| 6,174,332 B1 | 1/2001 | Loch et al. | |
| 6,183,512 B1 | 2/2001 | Howance, Jr. et al. | |
| 6,187,040 B1 | 2/2001 | Wright | |
| 6,217,610 B1 | 4/2001 | Carpentier et al. | |
| 6,231,602 B1 | 5/2001 | Carpentier et al. | |
| 6,283,993 B1 | 9/2001 | Cosgrove et al. | |
| 6,319,280 B1 | 11/2001 | Schoon | |
| 6,368,348 B1 * | 4/2002 | Gabbay | 623/2.36 |
| 6,406,492 B1 | 6/2002 | Lytle | |
| 6,416,548 B2 | 7/2002 | Chinn et al. | |
| 6,416,549 B1 | 7/2002 | Chinn et al. | |
| 6,528,107 B2 | 3/2003 | Chinn et al. | |
| 6,565,603 B2 | 5/2003 | Cox | |
| 6,602,289 B1 | 8/2003 | Colvin et al. | |
| 6,695,866 B1 | 2/2004 | Kuehn et al. | |
| 6,726,717 B2 | 4/2004 | Alfieri et al. | |
| 6,749,630 B2 | 6/2004 | McCarthy et al. | |
| 6,786,924 B2 | 9/2004 | Ryan et al. | |
| 6,797,002 B2 | 9/2004 | Spence et al. | |
| 6,805,710 B2 | 10/2004 | Bolling et al. | |
| 6,858,039 B2 | 2/2005 | McCarthy | |
| 6,908,482 B2 | 6/2005 | McCarthy et al. | |
| 6,955,689 B2 | 10/2005 | Ryan et al. | |
| 2001/0010018 A1 | 7/2001 | Cosgrove et al. | |
| 2001/0021874 A1 | 9/2001 | Carpentier et al. | |
| 2001/0034551 A1 | 10/2001 | Cox | |
| 2001/0041933 A1 | 11/2001 | Thoma | |
| 2001/0049557 A1 * | 12/2001 | Chinn | A61F 2/2445 623/2.36 |
| 2001/0049558 A1 | 12/2001 | Liddicoat et al. | |
| 2002/0129820 A1 * | 9/2002 | Ryan | A61F 2/2445 128/858 |
| 2002/0133180 A1 | 9/2002 | Ryan et al. | |
| 2002/0169503 A1 | 11/2002 | Lytle | |
| 2002/0173844 A1 | 11/2002 | Alfieri et al. | |
| 2003/0040793 A1 * | 2/2003 | Marquez | A61F 2/2445 623/2.36 |
| 2003/0045929 A1 | 3/2003 | McCarthy et al. | |
| 2003/0093148 A1 | 5/2003 | Bolling et al. | |
| 2003/0125715 A1 | 7/2003 | Kuehn et al. | |
| 2004/0006384 A1 | 1/2004 | McCarthy | |
| 2004/0088047 A1 | 5/2004 | Spence et al. | |
| 2004/0167619 A1 | 8/2004 | Case et al. | |
| 2005/0004666 A1 | 1/2005 | Alfieri et al. | |
| 2005/0021135 A1 | 1/2005 | Ryan et al. | |
| 2005/0043791 A1 | 2/2005 | McCarthy et al. | |
| 2005/0049698 A1 | 3/2005 | Bolling et al. | |
| 2005/0131533 A1 | 6/2005 | Alfieri et al. | |
| 2005/0182487 A1 | 8/2005 | McCarthy et al. | |
| 2005/0192666 A1 | 9/2005 | McCarthy | |
| 2005/0246014 A1 | 11/2005 | McCarthy | |
| 2005/0256567 A1 | 11/2005 | Lim et al. | |
| 2005/0256568 A1 | 11/2005 | Lim et al. | |
| 2005/0256569 A1 | 11/2005 | Lim et al. | |
| 2005/0267572 A1 | 12/2005 | Schoon et al. | |
| 2005/0278022 A1 * | 12/2005 | Lim | A61F 2/2445 623/2.36 |
| 2006/0015179 A1 | 1/2006 | Bulman-Fleming et al. | |
| 2006/0025856 A1 | 2/2006 | Ryan et al. | |
| 2006/0129236 A1 | 6/2006 | McCarthy | |
| 2006/0217803 A1 | 9/2006 | Ingle et al. | |
| 2006/0229708 A1 * | 10/2006 | Powell | A61B 17/00234 623/1.24 |
| 2007/0078468 A1 | 4/2007 | Ryan et al. | |
| 2007/0078514 A1 | 4/2007 | Ryan et al. | |
| 2007/0100441 A1 | 5/2007 | Kron et al. | |
| 2007/0156234 A1 | 7/2007 | Adzich et al. | |
| 2007/0191939 A1 | 8/2007 | Ryan et al. | |
| 2007/0276478 A1 | 11/2007 | Marmureanu et al. | |
| 2007/0299514 A1 * | 12/2007 | Colvin | A61F 2/2448 623/2.36 |
| 2009/0036979 A1 * | 2/2009 | Redmond | A61F 2/2445 623/2.36 |
| 2009/0149872 A1 * | 6/2009 | Gross | A61F 2/2445 606/151 |
| 2009/0177276 A1 * | 7/2009 | Carpentier | A61F 2/2448 623/2.36 |
| 2009/0248148 A1 * | 10/2009 | Shaolian | A61F 2/2448 623/2.37 |
| 2010/0076549 A1 * | 3/2010 | Keidar | A61F 2/2445 623/2.36 |
| 2010/0121437 A1 * | 5/2010 | Subramanian | A61F 2/2445 623/2.36 |
| 2010/0168845 A1 * | 7/2010 | Wright | A61F 2/2442 623/2.36 |
| 2011/0190879 A1 * | 8/2011 | Bobo | A61F 2/2445 623/2.37 |
| 2011/0238169 A1 * | 9/2011 | Jenson | A61F 2/2445 623/2.36 |
| 2013/0110231 A1 * | 5/2013 | Dobrilovic | A61B 17/0483 623/2.41 |
| 2013/0150958 A1 * | 6/2013 | De Paulis | A61F 2/2445 623/2.36 |
| 2013/0204361 A1 * | 8/2013 | Adams | A61F 2/2445 623/2.37 |
| 2013/0282110 A1 * | 10/2013 | Schweich, Jr. | A61F 2/243 623/2.11 |
| 2014/0081394 A1 * | 3/2014 | Keranen | A61F 2/2445 623/2.38 |
| 2014/0324163 A1 * | 10/2014 | Keranen | A61F 2/2409 623/2.36 |
| 2015/0012086 A1 * | 1/2015 | Bassin | A61F 2/2496 623/2.17 |
| 2015/0051698 A1 * | 2/2015 | Ruyra Baliarda | A61F 2/2448 623/2.36 |

FOREIGN PATENT DOCUMENTS

| | | |
|---|---|---|
| EP | 0 495 417 | 7/1992 |
| EP | 1 034 753 | 2/2005 |
| WO | 91/17721 | 11/1991 |
| WO | 94/18909 | 9/1994 |
| WO | WO 94/18909 | 9/1994 |
| WO | 99/04730 | 2/1999 |
| WO | 99/29269 | 6/1999 |
| WO | 99/49816 | 10/1999 |
| WO | 00/23007 | 4/2000 |
| WO | WO 00/23007 | 4/2000 |
| WO | 00/59408 | 10/2000 |
| WO | 00/62715 | 10/2000 |
| WO | 00/74603 | 12/2000 |
| WO | WO 00/74603 | 12/2000 |
| WO | 01/87191 | 11/2001 |
| WO | 02/074197 | 9/2002 |

(56) References Cited

FOREIGN PATENT DOCUMENTS

| WO | 03/020178 | 3/2003 |
|---|---|---|
| WO | 03/053289 | 7/2003 |
| WO | 2005/112830 | 12/2005 |
| WO | WO 2005/112830 | 12/2005 |

OTHER PUBLICATIONS

Ahmadi, A., et al., "Hemodynamic Changes Following Experimental Production and Correction of Acute Mitral Regurgitation With an Adjustable Ring Prosthesis," The Thoracic and Cardiovascular Surgeon, vol. 36, No. 6, pp. 313-319 (1988).
Alonso-Lei, "Adjustable Annuloplasty for Tricuspid Insufficiency," The Annals of Thoracic Surgery, (1988) 46(3), pp. 368-369.
Alonso-Lej, F., "The 'dynamic' mitral ring: A new concept in treating mitral insufficiency," Recent Progress in Mitral Valve Disease, pp. 45 and 443-449 (1984).
AnnuloFlex® and AnnuloFlo® Systems, Implantation techniques for mitral and tricuspid indications, CarboMedics (2003) (24 pages).
Belcher, J.R., "The Surgical Treatment of Mitral Regurgitation," British Heart Journal, vol. 26, pp. 513-523 (1964).
Bex J.P. and Lecompte Y., "Tricuspid valve repair using a flexible linear reducer," J. Cardiac Surg., 1:151 (1986).
Bolling, "Mitral Valve Reconstruction in the Patient with Heart Failure," Heart Failure Reviews, (2001) 6, pp. 177-185.
Bolling, S.F., "Mitral Reconstruction in Cardiomyopathy," The Journal of Heart Valve Disease, vol. 11, Suppl. 1, pp. S26-S31 (2002).
Bolling, S.F., et al., "Surgery for Acquired Heart Disease," The Journal of Thoracic and Cardiovascular Surgery, vol. 109, No. 4, pp. 676-683 (1995).
Bolling, et al., "Surgical Alternatives for Heart Failure," The Journal of Heart and Lung Transplantation, (2001) 20(7), pp. 729-733.
Carpentier, A., et al., "A New Reconstructive Operation for Correction of Mitral and Tricuspid Insufficiency," The Journal of Thoracic and Cardiovascular Surgery, vol. 61, No. 1, pp. 1-13 (1971).
Carpentier, A., "La Valvuloplastie Reconstitutive: Une Nouvelle Technique de Valvuloplastie Mitrale," Technique Chirugicale, No. 7, pp. 251-255 (1969).
Carpentier A., Deloche A., Hanania G., et al., "Surgical management of acquired tricuspid valve disease," J. Thorac. Cardiovasc. Surg., 67:53 (1974).
Carpentier, A.F., et al., "The 'Physio-Ring': An Advanced Concept in Mitral Valve Annuloplasty," Ann. Thorac. Surg., vol. 60, No. 5, pp. 1177-1186 (1995).
Carpentier-Edwards® Annuloplasty Rings (3 pages) (can be found in the file history for U.S. Appl. No. 10/918,503).
Carpentier-Edwards Physio™ Annuloplasty Ring (3 pages) (can be found in the file history for U.S. Appl. No. 10/918,503).
Castells, E., et al., "Long-Term Results with the Puig Massana-Shiley Annuloplasty Ring," The Journal of Cardiovascular Surgery, Abstracts, vol. 24, No. 4, p. 387 (1983).
Chachques, J.C., et al., "Absorbable Rings for Pediatric Valvuloplasty: Preliminary Study," Supplement IV to Circulation, vol. 82, No. 5, pp. IV-82-IV-88 (1990).
Cochran, et al., "Effect of Papillary Muscle Position on Mitral Valve Function: Relationship to Homografts," Ann. Thorac. Surg, (1998) 66:SS155-61.
Cooley, D.A., et al., "A Cost-Effective Dacron Annuloplasty Ring," The Annals of Thoracic Surgery, vol. 56, pp. 185-186 (1993).
Cooley, D.A., "Ischemic Mitral Insufficiency," Cardiac Surgery: State of the Art Reviews, vol. 6, No. 2, pp. 237-249 (1992).
Cooley, D.A., et al., "Mitral Leaflet Prolapse: Surgical Treatment using a Posterior Annular Collar Prosthesis," Cardiovascular Diseases Bulletin of the Texas Heart Institute, vol. 3, No. 4, pp. 438-443 (1976).
Cosgrove, D.M., III, et al., "Initial Experience with the Cosgrove-Edwards Annuloplasty System," The Annals of Thoracic Surgery, vol. 60, pp. 499-504 (1995).

Dagum et al., "Three-dimensional geometric comparison of partial and complete flexible mitral annuloplasty rings," The J. of Thorac. and Cardiovasc. Surg., vol. 122, No. 4 (2001).
Deloche, A., et al., "Valve Repair with Carpentier Techniques," The Journal of thoracic and Cardiovascular Surgery, vol. 99, No. 6, pp. 990-1002 (1990).
Department of Health & Human Services letter and attachments regarding file K926138, Carpentier-Edwards Physio™ Annuloplasty Ring, Model 4450 Mitral, dated Jun. 22, 1993 (295 pages).
Duran, C.G., et al., "Clinical and Hemodynamic Performance of a Totally Flexible Prosthetic Ring for Atrioventricular Valve Reconstruction," The Annals of Thoracic Surgery, vol. 22, No. 5, pp. 458-463 (1976).
Duran, C.G., "Reconstructive procedures of the Mitral Valve Including Ring Annuloplasty," Modern Technics in Surgery, 20 (1979).
Duran, C.G., et al., "Stability of Mitral Reconstructive Surgery at 10-12 Years for Predominantly Rheumatic Valvular Disease," Circulation Supplement I, vol. 78, No. 3, pp. I-91-I-96 (1988).
Durán, C.M.G., et al., "A New Absorbable Annuloplasty Ring in the Tricuspid Position: An Experimental Study," The Thoracic and Cardiovascular Surgeon, vol. 34, No. 6, pp. 377-379 (1986).
Duran, C.,M.G., et al., "Valve Repair in Rheumatic Mitral Disease," Supplement to Circulation, vol. 84, No. 5, pp. III 125-III 132 (1990).
Erk, M.K., "Morphological and Functional Reconstruction of the Mitral Valve: A New Annuloplastic Procedure," Texas Heart Institute Journal, vol. 9, pp. 329-334 (1982).
Erk, M.K., et al., "Semi-frame Mitral Annuloplasty," Cardiac Reconstructions pp. 157-163 (1989).
Flachskampf, et al., "Analysis of Shape and Motion of the Mitral Annulus in Subjects With and Without Cardiomyopathy by Echocardiographic 3-Dimensional Reconstruction," Journal of the American Society of Echocardiography, (2000) 13(4), pp. 277-287.
Freed, et al., "Prevalence and Clinical Outcome of Mitral-Valve Prolapse," The New England Journal of Medicine, (1999) 341(1), pp. 1-7.
Fundarò, P., et al., "Polytetrafluoroethylene Posterior Annuloplasty for Mitral Regurgitation," The Annals of Thoracic Surgery, Correspondence, vol. 50, No. 1, pp. 165-166 (1990).
Galler M. Kronzon I, Slater J., et al., "Long-term follow-up after mitral valve reconstruction: incidence of post-operative left ventricular out flow obstruction," Circulation, 74:I-99 (1986).
Gatti, et al., "Preliminary experience in mitral valve repair using the Cosgrove-Edwards annuloplasty ring," Interact Cardiovasc Thorac Surg, (2003) 2:256-261.
Ghosh, P.K., "Mitral Annuloplasty: A Right-Side View," The Journal of Heart Valve Disease, vol. 5, pp. 286-293 (1996).
Gorman, et al., "Dynamic Three-Dimensional Imaging of the Mitral Valve and Left Ventricle by Rapid Sonomicrometry Array Localization," J Thorac Card Surg, 112(3), (1996) pp. 712-726.
Gorman, et al., "The Effect of Regional Ischemia on Mitral Valve Annular Saddle Shape," Ann Thorac Surg (2004) 77, pp. 544-548.
Gorton, M.E., et al., "Mitral Valve Repair Using a Flexible and Adjustable Annuloplasty Ring," The Annals of Thoracic Surgery, vol. 55, pp. 860-863 (1993).
Gregori, F., et al., "Mitral Valvuloplasty with a New Prosthetic Ring," Official Journal of the European Association for Cardio-thoracic Surgery, vol. 8, No. 4, pp. 168-172 (1994).
Gregori, F., Jr., et al., "Um Novo Modelo De Anel Protetico Para Pacientes Com Insuficiencia Valvar Mitral. Relato de Dois Casos," Arquivos Brasileiros de Cardiologia, vol. 50, No. 6, pp. 417-420 (1988).
Haverich, et al., "Experimental and Clinical Experiences with Double-velour Woven Dacron Prostheses," Thorac. Cardiovasc. Surgeon 34 (1986) pp. 52-53.
Hendren, W.G., et al., "Mitral Valve Repair for Ischemic Mitral Insufficiency," The Annals of Thoracic Surgery, vol. 52, pp. 1246-1252 (1991).
Henze, A., et al., "The Adjustable Half-Moon: An Alternative Device for Tricuspid Valve Annuloplasty," Scandinavian Journal of Thoracic and Cardiovascular Surgery, vol. 18, pp. 29-32 (1984).
Jimenez, et al., "Effects of a Saddle Shaped Annulus on Mitral Valve Function and Chordal Force Distribution: An In Vitro Study," Annals of Biomedical Engineering, (2003) vol. 31, pp. 1171-1181.

(56) References Cited

OTHER PUBLICATIONS

Kasegawa, H., et al., "Physiologic Remodeling Annuloplasty to Retain the Shape of the Anterior Leaflet: A New Concept in Mitral Valve Repair," The Journal of Heart Valve Disease, vol. 6, pp. 604-607 (1997).
Katz, N.M., "Current Surgical Treatment of Valvular Heart Disease," American Family Physician, vol. 52, No. 2, pp. 559-568 (1995).
Kaye, D.M., et al., "Feasibility and Short-Term Efficacy of Percutaneous Mitral Annular Reduction for the Therapy of Heart Failure—Induced Mitral Regurgitation," Circulation, Brief Rapid Communication, No. 108, pp. 1795-1797 (2003).
Kurosawa, H., et al., "Mitral Valve Repair by Carpentier-Edwards Physio Annuloplasty Ring," the Japanese Journal of Thoracic and Cardiovascular Surgery, vol. 47, pp. 355-360 (1999).
Lachmann, J., M.D., et al., "Mitral Ring Annuloplasty: An Incomplete Correction of Functional Mitral Regurgitation Associated with Left Ventricular Remodeling," Current Cardiology Reports, vol. 3, pp. 241-246 (2001).
Levin et al., "Three-Dimensional Echocardiographic Reconstruction of the Mitral Valve, With Implications for the Diagnosis of Mitral Valve Prolapse," Circulation, 1989; 80(3):589-598.
Levine, R.A., et al., "The Relationship of Mitral Annular Shape to the Diagnosis of Mitral Valve Prolapse," Circulation, vol. 75, No. 4, pp. 756-767 (1987).
Martin, S.L., et al., "Echocardiographic Evaluation of Annuloplasty Rings: Comparison of Continuity Equation and Pressure Half-Time Methods," Journal of The American Society of Echocardiography, vol. 5, No. 3, p. 322 (1992).
Medtronic® Sculptor™ Annuloplasty Ring brochure, Medtronic Inc. (1993) (6 pages).
Melo, et al., "Atrioventricular Valve Repair Using Externally Adjustable Flexible Rings," The Journal of Thoracic and Cardiovascular Surgery, (1995) 110(5), pp. 1333-1337.
Melo, J.Q., et al., "Surgery for Acquired Heart Disease: Atrioventricular Valve Repair using Externally Adjustable Flexible Rings," The Journal of Thoracic and Cardiovascular Surgery, No. 110, pp. 1333-1337 (1995).
Miller, "Ischemic mitral regurgitation redux—To repair or to replace?" The Journal of Thoracic and Cardiovascular Surgery, (2001) 122(6), pp. 1059-1062.
Morse, D., et al., "Cardiac Valve Identification Atlas and Guide," Chapter 10 in Guide to Prosthetic Cardiac Valves, edited by Dryden Morse, Robert M. Steiner, and Javier Fernandez, Springer-Verlag New York Inc. (1985).
Murphy, J.P., et al., "The Puig-Massana-Shiley Annuloplasty Ring for Mitral Valve Repair: Experience in 126 Patients," The Annals of Thoracic Surgery, vol. 43, pp. 52-58 (1987).
Ogus, T.N., et al., "Posterior Mitral Annuloplasty with an Adjustable Homemade Ring," Journal of Cardiac Surgery, vol. 17, No. 3, pp. 226-228 (2002).
Pellegrini, A., et al., "Posterior Annuloplasty in the Surgical Treatment of Mitral Insufficiency," The Journal of Heart Valve Disease, vol. 2, pp. 633-638 (1993).
Reece, I.J., et al., "Surgical Treatment of Mitral Systolic Click Syndrome: Results in 37 Patients," The Annals of Thoracic Surgery, vol. 39, No. 2, pp. 155-158 (1985).
Rubenstein, F., et al., "Alternatives in Selection of Rings for Mitral Annuloplasty," Current Opinion in Cardiology, vol. 16, No. 2, pp. 136-139 (2001).
Salati, M., et al., "Annular Remodeling with Pericardial Reinforcement: Surgical Technique and Early Results," The Journal of Heart Valve Disease, vol. 2, pp. 639-641 (1993).
Salati, M., et al., "Posterior Pericardial Annuloplasty: A Physiocological Correction?", European Journal of Cardio-Thoracic Surgery, vol. 5, pp. 226-229 (1991).
Salvador, L., et al., "The Pericardium Reinforced Suture Annuloplasty: Another Tool Available for Mitral Annulus Repair," Journal of Cardiac Surgery, vol. 8, pp. 79-84 (1993).
Sato, et al., "The Biologic Fate of Dacron Double Velour Vascular Prostheses—A Clinicopathological Study," Japanese Journal of Surgery, (1989) 19(3), pp. 301-311.
Seguin, et al., "Advance in Mitral Valve Repair Using a Device Flexible in Three Dimensions," ASAIO Journal (1996), 42:M368-M371.
Shumway, S.J., et al., "A 'Designer' Annuloplasty Ring for Patients with Massive Mitral Annular Dilation," The Annals of Thoracic Surgery, vol. 46, No. 6, pp. 695-696 (1988).
Smolens, I., et al., "Current Status of Mitral Valve Reconstruction in Patients with Dilated Cardiomyopathy," Ital. Heart J., vol. 1, No. 8, pp. 517-520 (2000).
Smolens, et al., "Mitral valve repair in heart failure," The European Journal of Heart Failure, (2000) 365-371.
Tsakiris, A.G., "The psysiology of the mitral valve annulus," in The Mitral Valve-apluridisciplinary Approach, ed Kalmanson D. Publishing Sciences Group, Acton, Mass., p. 21 (1976).
Victor, S., et al., "Truly Flexible D-Shaped Autogenous Pericardial Ring for Mitral Annuloplasty," The Annals of Thoracic Surgery, vol. 56, pp. 179-180 (1993).
Vongpatanasin, W., et al., "Prosthetic Heart Valves," The New England Journal of Medicine, vol. 335, No. 6, pp. 407-416 (1996).
Parish, et al., "The Dynamic Anterior Mitral Annulus," The Society of Thoracic Surgeons, (2004) pp. 1248-1255.
Timek, et al., "Annular Height-to-Commissural Width Ratio of Annuloplasty Rings In Vivo," Circulation, (2005);112[suppl I]:I-423-I-428.
Glasson, et al., Three-Dimensional Regional Dynamics of the Normal Mitral Annulus During Left Ventricular Ejection, Journal of Thoracic and Cardiovascular Surgery, vol. 111, No. 3, (1996), pp. 574-585.
Glasson, et al., "Three-Dimensional Dynamics of the Canine Mitral Annulus During Ischemic Mitral Regurgitation," Society of Thoracic Surgeons, (1996), pp. 1059-1068.
Tibayan, et al., "Annular Remodeling in Chronic Ischemic Mitral Regurgitation: Ring Selection Implications," Society of Thoracic Surgeons, (2003), pp. 1549-1555.
Hasenkam, et al., "What force can the myocardium generate on a prosthetic mitral valve ring? An animal experimental study," Journal of Heart Valve Dis. (1994), 1 pg., found on website: http://www.ncbi.nlm.nih.gov/sites/entrez?cmd=Retrieve&db=PubMed&list_uids=8087273&dopt=Citation.
St. Jude Medical® Rigid Saddle Ring with EZ Suture™ Cuff, 4 pgs., printed Sep. 2007, found on website: http://www.sjm.com/devices/device.aspx?name=St.+Jude+Medical%26%23174%3B+Rigid+Saddle+Ring+with+EZ+Suture%26%23153%3B+Cuff&location=us&type=23.
Salgo, et al., "Effect of Annular Shape on Leaflet Curvature in Reducing Mitral Leaflet Stress," Circulation, (2002); 106:711-717.
Co-pending, U.S. Appl. No. 11/809,221, filed May 31, 2007, entitled "Annuloplasty Prosthesis With In Vivo Shape Identification and Related Methods of Use," in the name of Stephen B. Colvin et al.
Lawrence, et al., "A Biomechanical Analysis of Suture Materials and Their Influence on a Four-Strand Flexor Tendon Repair," The Journal of Hand Surgery, vol. 30, No. 4, 2005, pp. 836-841.
US 6,197,052, 03/2001, Cosgrove et al. (withdrawn)
US 6,673,110, 01/2004, Alfieri et al. (withdrawn)

\* cited by examiner

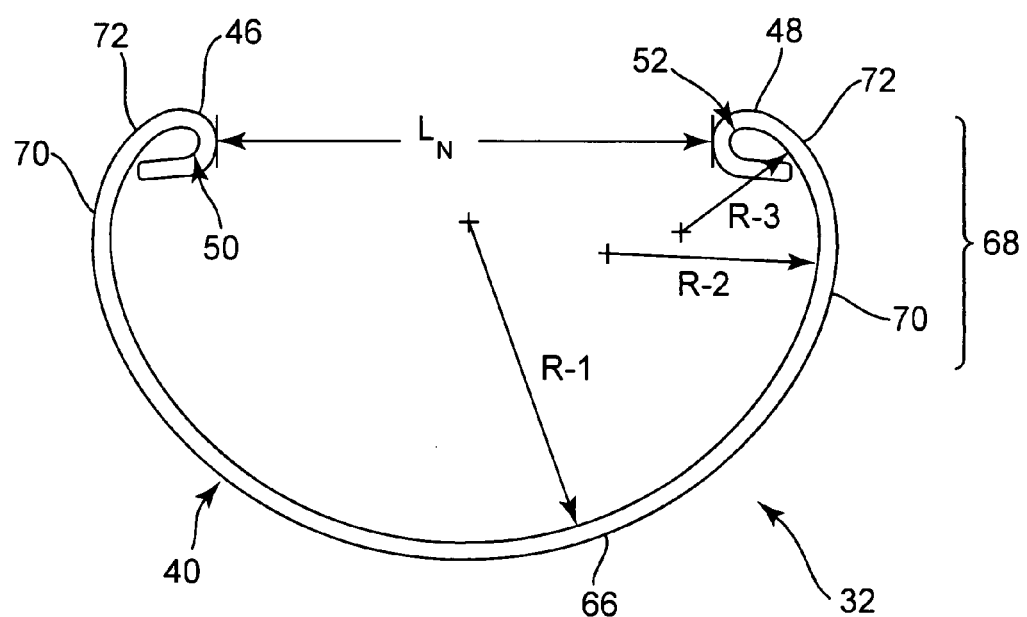
Fig. 3
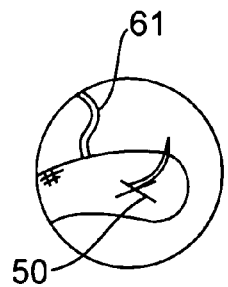 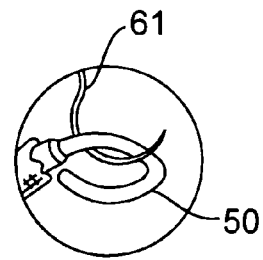
Fig. 4                Fig. 5

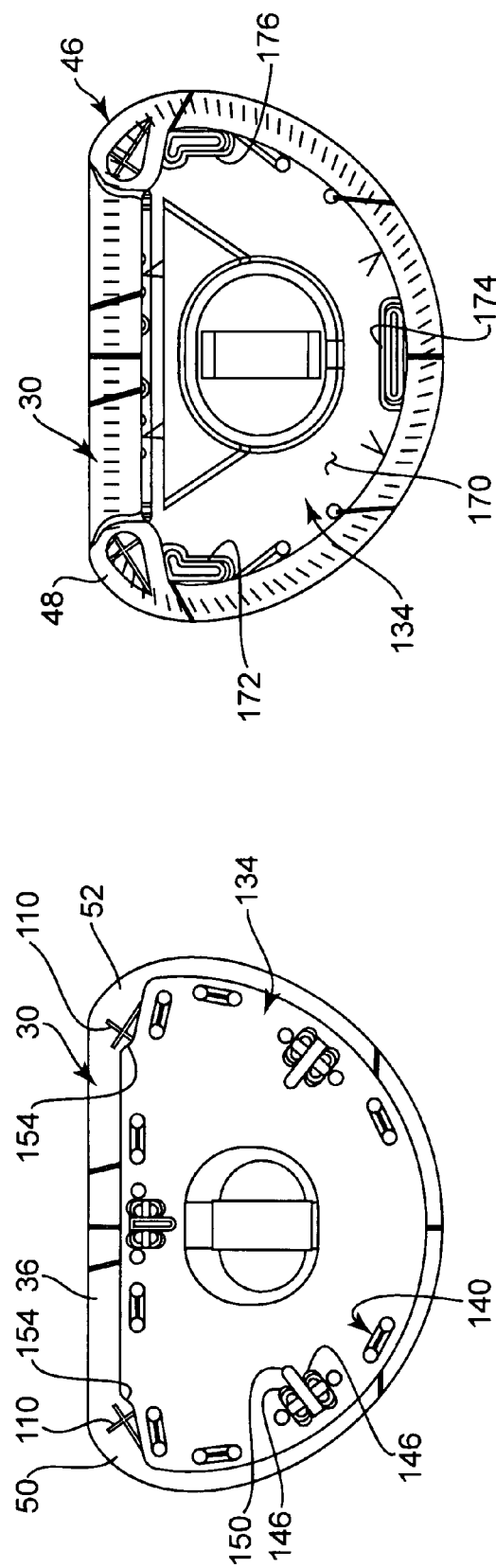
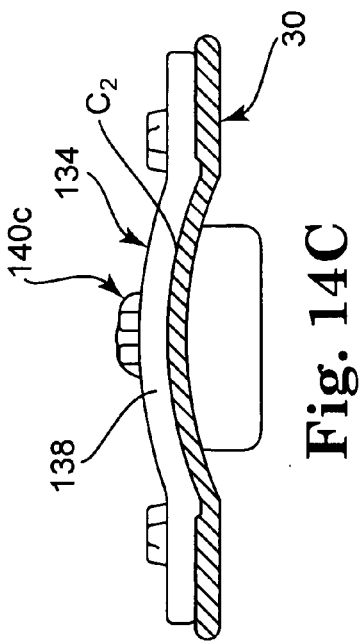
Fig. 14A
Fig. 14B
Fig. 14C

ANNULOPLASTY RING AND METHOD

PRIORITY CLAIM

This application claims the benefit of U.S. Provisional Patent Application having Ser. No. 60/810,600, filed on Jun. 2, 2006, entitled "ANNULOPLASTY RING AND METHOD," the entire disclosure of which is incorporated herein by reference for all purposes.

BACKGROUND

The present invention relates generally to annuloplasty prostheses and methods for repair of heart valves. More particularly, it relates to annuloplasty rings, and related instruments and procedures, for surgically reconstructing a valve annulus of a patient's heart, for example a mitral valve annulus.

Annuloplasty prostheses, generally categorized as either annuloplasty rings or annuloplasty bands, are employed in conjunction with valvular reconstructive surgery to assist in the correction of heart valve defects such as stenosis and valvular insufficiency. There are two atrio-ventricular valves in the heart. The mitral valve is located on the left side of the heart, and the tricuspid valve is located on the right side. Anatomically speaking, each valve type forms or defines a valve annulus and valve leaflets. To this end, the mitral and tricuspid valves differ significantly in anatomy. For example, the annulus of the mitral valve is somewhat "D" shaped, whereas the annulus of the tricuspid valve is more nearly circular.

Both valves can be subjected to or incur damage that requires the valve in question be repaired or replaced. The effects of valvular dysfunction vary. For example, mitral regurgitation, a complication of end-stage cardiomyopathy, has more severe physiological consequences to the patient as compared to tricuspid valve regurgitation. Regardless, many of the defects are associated with dilatation of the valve annulus. This dilatation not only prevents competence of the valve, but also results in distortion of the normal shape of the valve orifice. Remodeling of the annulus is therefore central to most reconstructive procedures on the mitral valve. In this regard, clinical experience has shown that repair of the valve, when technically possible, produces better long-term results as compared to valve replacement.

Many procedures have been described to correct the pathology of the valve leaflets and their associated chordae tendinae and papillary muscles. For example, with respect to the mitral valve, it is a bicuspid valve having a large posterior leaflet that coapts or meets with a smaller anterior leaflet. The part of the mitral valve annulus that is attached to the anterior leaflet is called the anterior aspect, while the part attached to the posterior leaflet is called the posterior aspect. There are two fibrous trigones that nearly straddle the anterior aspect. With this in mind, in mitral repairs, it is considered important to preserve the normal distance between the two trigones. A significant surgical diminution of the inter-trigonal distance may cause left ventricular outflow obstruction. Thus, it is desirable to maintain the natural inter-trigonal distance during and following mitral valve repair surgery.

Consequently, when a mitral valve is repaired surgically, the result is generally a reduction of the size of the posterior aspect of the mitral valve annulus. As part of a typical mitral valve repair, an annulus is diminished (i.e., constricted) so that the leaflets may coapt correctly upon closing of the valve, or an annulus or segment thereof (e.g., anterior or posterior aspect) is stabilized to prevent post-operative dilatation from occurring, either as frequently achieved by implantation of a prosthetic ring or band in a supra annular position. The purpose of a ring or band is to restrict and/or support an annulus to correct and/or prevent valvular insufficiency. However, it is important not to overly restrict an annulus as an unacceptable valvular stenosis may result. In tricuspid valve repair, constriction of an annulus usually takes place by positioning a band partially about the posterior leaflet segment and a small portion of the adjacent anterior leaflet segment. The septal leaflet segment is not usually required to be shortened.

As described above, both annuloplasty rings and annuloplasty bands are available for repair of an atrio-ventricular valve. Examples of annuloplasty rings are shown in U.S. Pat. Nos. 5,306,296; 5,669,919; 5,716,397; and 6,159,240, the teachings of which are incorporated herein by reference. In general terms, annuloplasty rings completely encompass both the anterior and posterior aspects of a valve annulus, and have either a rigid (or semi-rigid) design, or a flexible design. Annuloplasty bands, on the other hand, are specifically designed to primarily encompass only a portion of the valve annulus. With the rigid or semi-rigid configuration, an annuloplasty ring serves to remodel the dysfunctional valve annulus to a desired shape such as that which would mimic the normal systolic shape of the valve. In this regard, and relative to the mitral valve, recent studies have identified that the healthy mitral valve annulus has a natural saddle shape that becomes exaggerated in systole. Efforts have been made to provide a rigid annuloplasty ring that more closely mimics this saddle shape, for example as shown in U.S. Pat. No. 6,858,039 and U.S. Publication No. 2003/0093148, the teachings of which are incorporated herein by reference. While viable, this remodeling/rigid annulus support may overtly restrict natural movement of the mitral valve annulus when functioning during diastole and systole, especially in the mitral valve anterior aspect as suggested by Parrish, L. M., et al., *The Dynamic Anterior Mitral Annulus*, (Annals. of Thoracic Surgery 2004; 78:1248-55).

While the suggested saddle-shaped annuloplasty rings may assist in achieving valve annulus remodeling that more closely mimics the natural shape of a healthy valve annulus, other concerns may arise. For example, it is difficult to accurately estimate whether any saddle-shaped annuloplasty ring is of an appropriate size for the valve to be repaired. In particular, conventional annuloplasty ring implantation procedures entail initially performing a cardiac bypass operation, followed by use of a sizing instrument to estimate a size of the valve annulus in question. In general terms, a surgeon will have available to him or her a number of differently sized annuloplasty rings, along with a number of sizer bodies each having a size and shape corresponding with a respective one of the annuloplasty rings on hand. Because a heart is flaccid during cardiac bypass, a valve annulus in question will be in a diastolic shape (e.g., essentially non-saddled or flat). In contrast, a saddled annuloplasty ring, and thus a corresponding sizer body, reflects the systolic end shape of the valve annulus. Thus, comparing a saddle-shaped sizer body with a valve annulus in a relatively flat, diastolic end state may not provide an accurate sizing estimate. In addition, the suggested saddle-shaped mitral valve annuloplasty rings may create leaflet tethering in dilated cardiomyopathy and ischemic mitral regurgitation applications. Further, where an annuloplasty ring is shaped to rigidly or semi-rigidly remodel the valve annulus to the saddle shape associated with the systolic end state, the existing leaflets may be distorted; further, the annuloplasty ring is subjected to significant forces as the valve transitions between the systolic and diastolic states, potentially leading to long-term annuloplasty ring degradation from fatigue, such as fracturing or dehiscence.

In contrast to annuloplasty rings, annuloplasty bands are specifically designed to primarily encompass only a portion of a valve annulus. For example, a mitral valve annuloplasty band is typically configured to encompass only the posterior aspect of a mitral valve annulus, thus promoting natural movement of the anterior aspect. Examples of annuloplasty bands are shown in U.S. Pat. Nos. 5,824,066 and 6,786,924, and PCT International Patent Publication No. WO00/74603, the teachings of which are incorporated herein by reference. While quite viable, annuloplasty bands may present other concerns. First, the profile (e.g., thickness) of some annuloplasty bands may theoretically be sufficiently large so as to restrict or disturb blood flow. Also, an annuloplasty band may not provide sufficient restriction to possible dilatation of a valve annulus aspect(s) otherwise not encompassed by the band (e.g., the anterior aspect of the mitral valve annulus). Ischemic mitral regurgitation and dilated cardiomyopathy are two examples of clinical applications of these phenomena that might otherwise indicate a potential for anterior dilatation.

In light of the above, a need exists for improved annuloplasty ring designs, and related surgical instruments and techniques that more accurately reflect both the shape and functioning of a healthy valve annulus, such as a mitral valve annulus.

SUMMARY

Some aspects in accordance with principles of the present invention relate to an annuloplasty ring for repairing an atrioventricular valve having a valve annulus. The ring includes a sheath, an arcuate stiffening element, and a tensioning member. The arcuate stiffening element is disposed within the sheath and defines discrete, first and second ends separated by a lateral spacing. The tensioning member extends along the lateral spacing between the ends of the stiffening element. In this regard, the tensioning member is characterized as being more flexible than the stiffening element, and is configured to provide a taut state. In the taut state, the tensioning member is substantially non-extensible and impedes expansion of the lateral spacing between the first and second ends of the stiffening member when the annuloplasty ring is subjected to an external force. With this configuration, then, the stiffening element serves to remodel a valve annulus to a desired shape, while the tensioning member exhibits sufficient flexibility to allow for natural movement of a valve annulus while limiting (in the taut state) the extent of annular dilatation (e.g., overt lateral separation of the first and second ends of the stiffening element) due to in vivo forces. It also allows the anterior aspect to assume its natural systolic saddle shape. In some embodiments, the tensioning member is configured to provide flexibility in all directions except extension. In other embodiments, the tensioning member is configured such that in the taut state, the lateral spacing between the first and second ends increases by no more than 0.2 inch when the annuloplasty ring is subjected to a lateral tensile load or force of one pound. In other embodiments, the tensioning member includes a suture looped between the first and second ends of the stiffening element to define a plurality of segment links.

Other aspects in accordance with principles of the present invention relate to a combination annuloplasty ring and holder for use by a surgeon in conjunction with annuloplasty surgery performed on a patient's heart valve defining a valve annulus. The combination includes an annuloplasty ring and a holder. The annuloplasty includes a sheath, an arcuate stiffening element, and a tensioning member. The arcuate stiffening element is disposed within the sheath and defines discrete, first and second ends that are separated by a lateral spacing. The tensioning member extends along the lateral spacing between the stiffening member ends, and is characterized as being more flexible than the stiffening element. Further, the tensioning member is configured to provide a taut state in which the tensioning member is substantially non-extensible and impedes expansion of the lateral spacing between the first and second ends of the stiffening element. The holder selectively maintains the annuloplasty ring and includes a ring-retaining plate. The plate preferably forms a first curvature in a first plane corresponding generally to a curvature of the stiffening element, and a second curvature in a second plane differing from the first plane. Upon final assembly, the annuloplasty ring is applied to the ring-retaining plate such that a first segment of the ring (corresponding with the stiffening element) is assembled to the first curvature and a second segment of the ring (corresponding with the tensioning member) is mounted to the second curvature of the ring-retaining plate. As such, the ring-retaining plate maintains the second segment of the annuloplasty ring, and thus the tensioning member, in a curved orientation. In some embodiments, the second plane is generally perpendicular to the first plane, such that when applied to the ring-retaining plate, the annuloplasty ring assumes a saddle-shape. In other embodiments, the ring-retaining plate is flat and maintains the annuloplasty ring in a flat shape.

Yet other aspects in accordance with principles of the present invention relate to an annuloplasty ring for implantation in a mitral valve annulus for repairing the mitral valve. The annuloplasty ring includes a sheath, an arcuate stiffening element, and a tensioning member. The arcuate stiffening element is disposed within the sheath and defines discrete, first and second ends separated by a lateral spacing. The tensioning member extends along the lateral spacing between the ends of the stiffening member, and is characterized as being more flexible than the stiffening member. With this in mind, the ring defines an anterior segment along a region corresponding with the tensioning member, and a posterior segment along a region corresponding with the stiffening element. The anterior segment is adapted to be implanted on an anterior aspect of the mitral valve annulus, whereas the posterior segment is adapted to be implanted on a posterior aspect of the mitral valve annulus. Finally, the stiffening element is adapted to remodel the posterior aspect of the mitral valve annulus and the tensioning member is configured to conform to a natural anatomy of the anterior aspect.

BRIEF DESCRIPTION OF THE DRAWINGS

FIG. 3 is a top view of a stiffening element employed in the annuloplasty ring of FIG. 1;

FIG. 4 is an enlarged view of a portion of FIG. 1 illustrating a mark that is provided to indicate the location of an underlying eyelet on the annuloplasty ring;

FIG. 5 is a view similar to FIG. 4 with portions of the fabric sheath broken away to show the eyelet;

FIG. 14A is a top view of the assembled annuloplasty ring/ring-retaining plate of FIG. 13;

FIG. 14B is a bottom view of the assembly of FIG. 14A;

FIG. 14C is an end view of the assembly of FIG. 14A;

DETAILED DESCRIPTION

Figure 1:
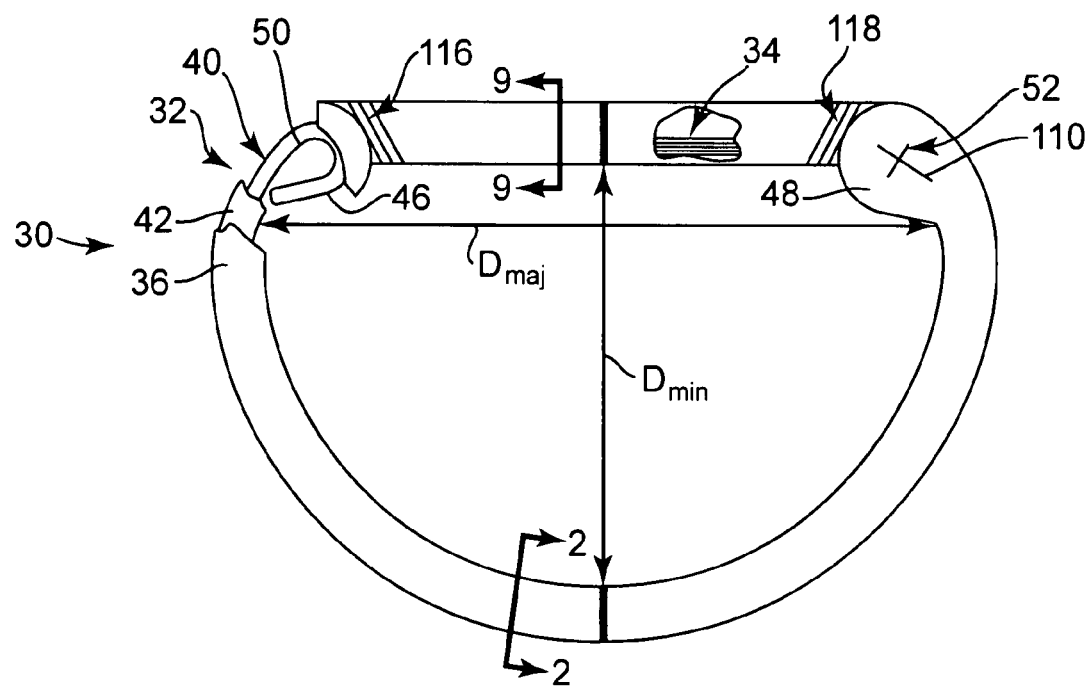
FIG. 1 is a top view of an annuloplasty ring in accordance with principles of the present invention, with portions peeled away.

An annuloplasty ring 30 in accordance with aspects of principles of the present invention is illustrated in FIG. 1. The annuloplasty ring 30 is particularly adapted to repair one of the atrio-ventricular valves, such as the mitral and tricuspid valves. As a point of reference, the annuloplasty ring 30 illustrated in FIG. 1 is configured for mitral valve annulus repair, it being understood that other shapes may be incorporated for other valve annulus anatomies (e.g., the tricuspid valve annulus). Thus, the present invention is not limited to mitral valve annuloplasty.

The annuloplasty ring 30 includes a stiffening element 32, such as a stiffening wire, a tensioning member 34, and a fabric sheath 36 encompassing the stiffening element 32 and the tensioning member 34. Details on the various components are provided below. In general terms, however, the stiffening element 32 imparts an arcuate shape to the annuloplasty ring 30, and is adapted to remodel the valve annulus (not shown) in question to a desired shape and/or size. The tensioning member 34 functions to limit separation of ends of the stiffening element 32 (described below) by virtue of being limited to extend under a tensile force and preferably extends between ends of the stiffening element 32, and is characterized as being more flexible than the stiffening element 32. Such flexibility is created by potentially allowing the tensioning member 34 to be shaped when implanted and to permit compressive movement (i.e., such as when the ends of the stiffening element 32 are flexed toward one another) but to limit flexure of the stiffening element 32 where its ends move away from one another beyond a determined limit that may be zero or greater. Thus, the tensioning member 34 is capable of moving with movement of the valve annulus following implantation, conforming to natural annulus functioning.

Further, the tensioning member 34 provides a taut state in which the tensioning member 34 is substantially non-extensible, thus serving to impede overt dilatation of the stiffening element 32/annuloplasty ring 30. As such, the tensioning member 34 serves to resist loads or forces that might otherwise tend to open or dilate the annuloplasty ring 30, such as loads encountered in vivo due to valve dilatation.

In some embodiments, the stiffening element 32 is akin to the stiffening element embodiments described in U.S. Pat. No. 6,786,924, the teachings of which are incorporated herein by reference. With this in mind, and with additional reference to FIG. 2, the stiffening element 32 can be or includes a stiffening wire 40 that in one embodiment is overmolded with a biocompatible, biostable, implantable, medical grade elastomeric protective coating 42, such as elastomeric thermoplastic polymers (e.g., polyurethane) or silicone (e.g., liquid silicone rubber (LSR)). Alternatively, the protective coating 42 can be tubing within which the stiffening wire 40 is disposed, the tubing consisting of biocompatible, biostable, implantable, medical grade elastomeric material such as elastomeric thermoplastic polymers (e.g., polyurethane) or silicone elastomeric. In yet other embodiments, the protective coating 42 can be eliminated.

As shown in FIG. 3, the stiffening element 32 (e.g., the stiffening wire 40) defines discrete, first and second ends 46, 48, and in some embodiments includes eyelets 50, 52 at the first and second ends 46, 48, respectively. For example, where the stiffening element 32 is formed by or includes the wire 40, the opposite ends 46, 48 of the wire 40 can be bent back onto itself to form the eyelet 50, 52, with the stiffening element 32 consisting of a single length of wire. As used herein, "eyelet" means an opening with a substantially closed perimeter, but does not require a specific shape (e.g., an eyelet can be round, square rectangular, trapezoidal, hexagonal, tear-drop, oval, elliptical, or any other suitable shape, although shapes with lower stress concentration and rounded features are generally preferred). In embodiments in which the stiffening element 32 includes the wire 40, there will be, for example, about a 0.5 mm gap along the perimeter of the eyelets 50, 52 due to spring back of the wire 40 after forming the respective eyelets 50, 52. Regardless, and as illustrated in FIGS. 4 and 5, the eyelets 50 and 52 are adapted to receive at least one suture 61 to secure the annuloplasty ring 30 to a valve annulus (not shown) of a heart valve, such as a mitral valve, tricuspid valve, etc. Alternatively, however, the stiffening element 32 can assume other configurations, and need not include one or both of the eyelets 50 and/or 52. Another alternative is that the eyelets can be added by one or more additional components.

Available shapes for the stiffening element 32 are described in greater detail below. In general terms, however, the stiffening element 32 is preferably shaped to match the native or natural shape of a valve annulus in which an annuloplasty ring 30 is to be applied at least with respect to the desired size of a modified or corrected annulus or portion thereof. Thus, the stiffening element 32 can be generally shaped to mimic the native natural mitral valve posterior annulus anatomy (i.e., generally symmetrical, horseshoe-like shape) for mitral valve annulus repair; can be generally shaped and mimicked in native natural tricuspid valve annulus anatomy (i.e., non-symmetrical offset curve); etc.

Returning to FIG. 3, some embodiments in which the annuloplasty ring 30 is adapted for repairing of a mitral valve (not shown), the arcuate shape of the stiffening element 32 is configured to match the natural posterior aspect anatomy of the mitral valve annulus. More particularly, the annuloplasty ring 30 is preferably configured such that after implant, the stiffening element 32 extends from the point adjacent the antero-lateral trigone, past the posterior leaflet with the second end 48 adjacent the postero-medial trigone. Further, the eyelets 50, 52 (where provided) can be positioned and adapted to be secured to the valve annulus at the antero-lateral trigone and the postero-medial trigone, and are preferably sufficiently large to encompass both trigone and adjacent commissure so that the first eyelet 50 can be positioned and maintained to encompass the inferior commissure at the valve annulus, and the second eyelet 52 can be positioned and maintained to encompass the superior commissure at the valve annulus. Regardless, the stiffening element 32 is configured to independently define and maintain the arcuate shape, with the discrete first and second ends 46, 48 being separated by a lateral spacing $L_N$ in a free or natural state. That is to say, in the absence of any external force or stress being placed upon the stiffening element 52, the ends 46, 48 are separated by the lateral spacing $L_N$.

Figure 6:
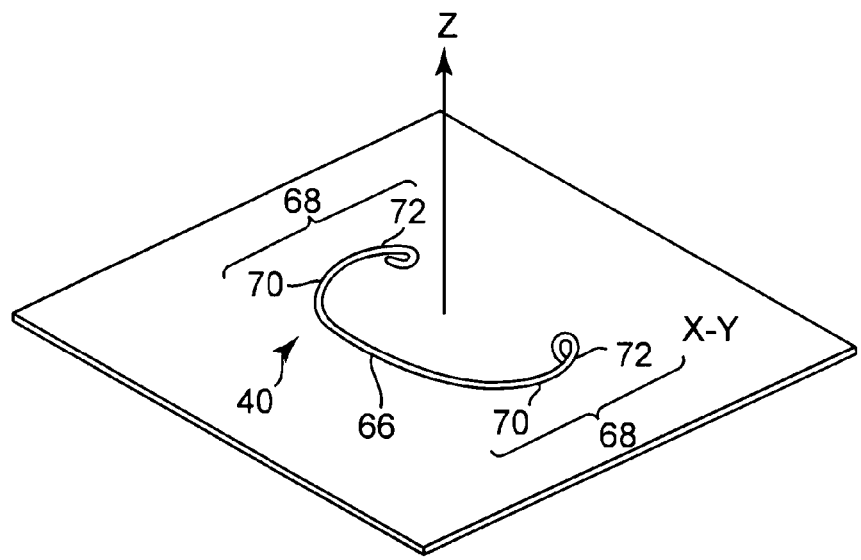
FIG. 6 is a perspective representation of one embodiment of a stiffening element in accordance with principles of the present invention relative to an X-Y plane and Z direction.
Figure 7:
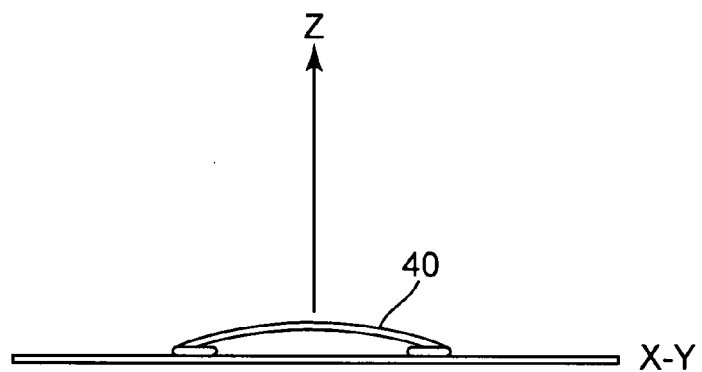
FIG. 7 is a side view of a stiffening element as shown in FIG. 6 in the X-Y plane and Z direction, illustrating an embodiment including a saddle-shaped curve in the Z direction.

FIG. 6 shows the annuloplasty ring 30 defined in two dimensions, which is relevant to the relatively flat, relaxed or flaccid annulus shape, for example, as occurs during surgery. FIG. 7 illustrates a three-dimensional shape of an embodiment of a stiffening wire 40, which is generally arcuate in an X-Y plane (e.g., C-shaped), and generally saddle-shaped in the Z direction. This configuration is also contemplated as may be incorporated into a flat shape as shown in FIG. 6, and generally can be designed to conform to the expected natural shape of the posterior aspect of the mitral valve annulus. With this configuration, the stiffening wire 40 forms a compound curve in the X-Y plane (see, e.g., FIGS. 3 and 6) including (a) an intermediate portion 66 having a first radius of curvature R1, and (b) opposite end portions 68 having a second radius of curvature R2, with the first radius of curvature R1 being greater than the second radius of curvature R2. For example, each of the opposite end portions 68, includes (i) a transition segment 70 extending outwardly from the intermediate portion 66, with the transition segment 70 having the second radius of curvature R2 in the X-Y plane; and (ii) an end segment 72 extending from the transition segment 70, the end segment 72 having a third radius of curvature R3 in the X-Y plane. In this one embodiment for mitral valve repair, the first radius of curvature R1 is greater than the second radius of curvature R2, and the second radius of curvature R2 is greater than the third radius of curvature R3. The preferred magnitude of each radius R1, R2, and R3 will vary within this constraint depending on the size of the mitral valve being repaired. Alternatively, the stiffening wire 40 can assume other shapes appropriate for mitral valve annulus repair that may or may not include one or more of the X-Y plane curvatures described above. Along these same lines, the stiffening wire 40/stiffening element 32 can provide a more pronounced or less pronounced curvature in the Z direction, and can define a compound curvature in the Z direction. Even further, the stiffening wire 40, and thus the stiffening element 32, can assume an entirely different shape, that may or may not include a saddle shape or Z direction component, such as may be desirable, for example with native tricuspid valve anatomy.

In addition to the shape of the stiffening element 32/stiffening wire 40 shown in FIG. 7, other shapes are possible. For example, the stiffening element 32 can be shaped to mimic the natural shape of a mitral valve in a systolic end state (i.e., when the mitral valve is closed). Alternatively, the stiffening element 32 can have a less pronounced saddle shape, reflecting a variation in height (i.e., curvature in the Z direction) corresponding to a mitral valve annulus shape between the natural systolic and diastolic end shapes. Once again, however, the stiffening element 32 can assume a wide variety of other shapes as desired by different ring designs as are presently known or later developed. Also, a variety of shapes are possible as allowed by the materials that comprise the ring.

In addition to providing the above shape characteristics described, the stiffening element 32 is also, in some embodiments, radiopaque, echogenic, and/or otherwise imaging enhanced so that it may readily be visualized after implantation using various existing techniques or any future developed techniques, including x-ray, MRI, echogram, etc. By "radiopaque," it is meant that the material or element prevents the passage of radiation. "Radiation" is meant to include electromagnetic energy, light, etc. By "echogenic," it is meant that it reflects sound waves. Metal wire, for example, is radiopaque. Where the stiffening element 32 includes or comprises the wire 40, the wire 40 can be formed of any medically-acceptable, implantable, biocompatible metal, such as MP35N alloy, titanium, stainless-steel, shape memory materials such as Nitinol™, or other similar inert biocompatible metal. For example, suitable wire is the wrought cobalt-35 nickel-20 chromium-10 molybdenum alloy identified as MP35N available from Carpenter Technology Corp., Wyomissing, PA. U.S. patent application, Ser. No. 11/809,221, entitled "ANNULOPLASTY PROSTHESIS WITH IN VIVO SHAPE IDENTIFICATION AND RELATED METHODS OF USE," and filed on even date as the present application, teaches an annuloplasty ring incorporating radiopaque, echogenic and/or other imaging enhancing elements, which are called "imaging elements." This reference is incorporated in its entirety herein by reference.

Alternatively, the stiffening element 32 may comprise (e.g., consist essentially of) a molded polymeric element. In these alternative embodiments, the molded polymeric element preferably includes a radiopaque coating or filler such as, but not limited to, barium sulphate, which is radiopaque with respect to electromagnetic energy. The eyelets 50, 52 (where provided) can be integrally molded with the rest of the stiffening element, or can be separately formed and subsequently assembled to the molded element.

Returning to FIG. 1, the tensioning member 34 extends between the first and second ends 46, 48 (referenced generally) of the stiffening element 32, and is characterized as being more flexible than the stiffening element 32. The tensioning member 34 is capable of moving with movement of a valve annulus following implantation, and conforming to natural annulus functioning, pursuant to the amount of flexibility thereby as preferably only limited as to extension beyond a determined limit. In addition, the tensioning member 34 limits or impedes dilatation of the annuloplasty ring 30, in particular lateral separation or movement of the first and second ends 46, 48 relative to one another, after reaching a taut state. Thus, the tensioning member 34 is substantially non-extensible in the taut state, allowing for flexibility only under loads that close (e.g., compress) or twist the annuloplasty ring 30 as described below.

The term "tensioning" with respect to the tensioning member 34 does not mean that the tensioning member actually applies tension to the annuloplasty ring 30, although it could. The tensioning member 34 primarily effectively limits separation of the first and second ends 46, 48 to keep them from separating when a taut state of the tensioning member 34 is achieved. In a free state, the tensioning member 34 may permit a determined amount of separation to increase flexibility and as a result of such flexibility, to permit greater shape to be assumed by it. Flexibility is also imparted to the tensioning member 34 to permit shape assumption by permitting the ends 46 and 48 to move toward one another, the effect of which is to reduce or eliminate tension on the tensioning member 34 and permit flexibility thereof. Movement of ends 46 and 48 toward one another can be as a result of valve annulus movement after implantation, or may be provided as part of the implantation process (i.e., by suturing the ring 30 in place). Such implantation can be controlled by use of a holder described below for desired shaping.

Figure 8:
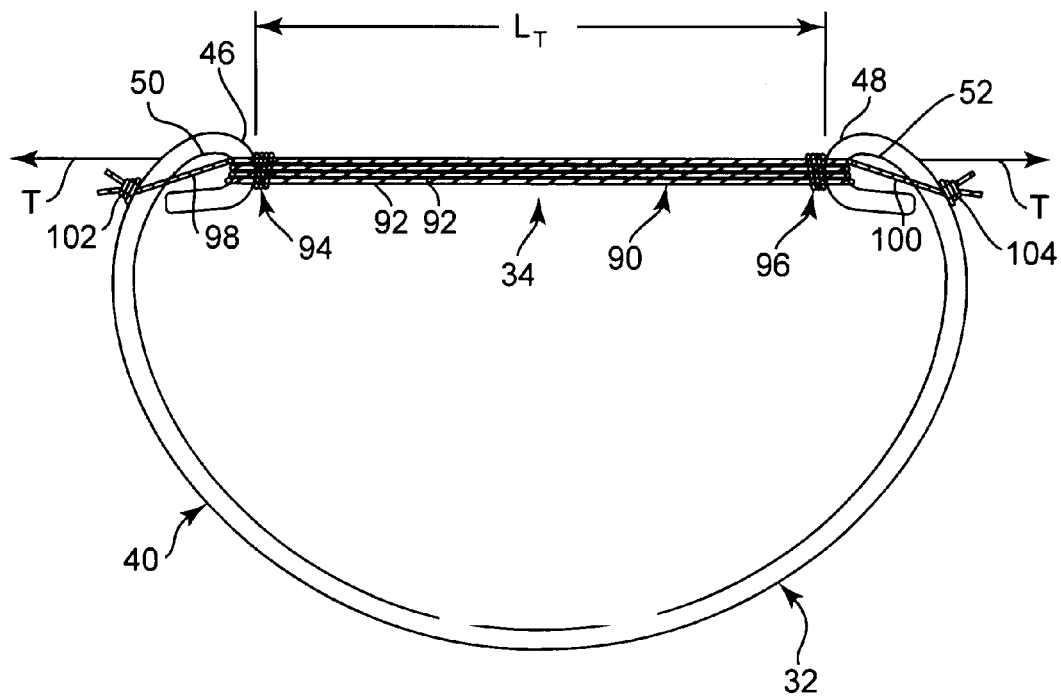
FIG. 8 is a top view of an embodiment of a tensioning member in accordance with principles of the present invention applied to a stiffening element employed with the annuloplasty ring of FIG. 1.

With the above general description in mind, FIG. 8 illustrates one embodiment of the tensioning member 34 applied to the stiffening element 32 otherwise in the form of the wire 40 bent back onto itself to form the eyelets 50, 52 at the first and second ends 46, 48, respectively. With this in mind, the one embodiment of a tensioning member 34 as illustrated in FIG. 8 is a suture 90 looped or wound between the first and second ends 46, 48, and in particular the eyelets 50, 52. With this wound construction, the suture 90 defines a plurality of segment links 92, for example five, seven, or nine segment links 92 (although a greater or lesser number of the links 92 can be formed or provided). The suture 90 is assembled to the stiffening element 32 so as to form first and second sliding knots 94, 96 interiorly adjacent a respective one of the eyelets 50, 52. Further, opposing end portions 98, 100 of the suture 90 are secured to the stiffening element 32 via securement knots 102, 104, respectively. In one embodiment, the sliding knots 94 and 96 are half-hitched knots that are self-tightening when the looped suture 90 is tensioned (i.e., a tensile load T tending to pull or force the first and second ends 46, 48 laterally away from one another). Alternatively, the sliding knots 94, 96 can assume a variety of other forms, and in some embodiments can be eliminated. Similarly, the securement knots 102, 104 can assume a variety of forms, but in one embodiment are square knots. The suture 90 can assume a variety of forms, and in some embodiments is a braided polyester 3-0 or 4-0 suture; alternatively, a larger suture size (e.g., 0 to 2-0) or smaller suture (e.g., 5-0 to 6-0) can be employed. In other embodiments, the tensioning member 34 has a similar general construction, but is formed of one or more substantially non-extensible polymer or fabric strands, metal wire strand(s), etc. In addition or alternatively, a plurality of sutures or other material strands can be provided. In yet other embodiments, the single suture 90 is secured to the stiffening element 32 via a single securement knot (i.e., one of the securement knots 102 or 104 is eliminated). In yet other embodiments, the tensioning member 34 can be secured to the stiffening element 32 using a variety of other techniques such as crimping, slip/press-fitting, adhesive, etc.

Regardless of an exact form or method of assembly, the tensioning member 34 is transitionable to the taut state reflected in FIG. 8. As a point of reference, and as previously described with respect to FIG. 3, the stiffening element 32 is formed of a rigid or semi-rigid material that naturally assumes the curved or arcuate shape. In this natural shape or state, the lateral spacing $L_N$ (FIG. 3) is established between the first and second ends 46, 48. With this in mind, and in some embodiments, the tensioning member 34 is assembled to the stiffening element 32 such that the tensioning member 34 is taut when the stiffening element 32 is in its natural state. In other words, a length $L_T$ of the segment links 92 corresponds with the natural lateral spacing $L_N$ such that the tensioning member 34 does not compress the ends 46, 48 toward one another. In other embodiments, the tensioning member 34 can be configured and/or assembled to the stiffening element 32 so as to tension or inwardly deflect the stiffening element 32, and in particular the first and second ends 46, 48, from the natural state. With this alternative construction, then, the tensioning member 34 slightly contracts the stiffening element 32 such that the first and second ends 46, 48 exist at a lateral spacing $L_T$ that is less than the natural lateral spacing $L_N$. The stiffening element 32 effectively applies a tensile load or force onto the tensioning member 34, thus ensuring that the tensioning member 34 is in the taut state under circumstances where the annuloplasty ring 30 is not otherwise subjected to other external forces. Conversely, the tensioning member 34 can be constructed and/or assembled to the stiffening element 32 such that when the stiffening element 32 is in the natural state, the tensioning member 34 is relatively loose (i.e., the length $L_T$ of the segment links 92 is greater than the natural lateral spacing $L_N$ established by the stiffening element 32 such that the segment links 92 are not under tension when the annuloplasty ring 30 (FIG. 1) is otherwise free of external forces). With this construction, then, the tensioning member 34 permits a controlled amount of expansion in the lateral spacing $L_N$ before the taut state is achieved. Regardless, and as described in greater detail below, the tensioning member 34 exhibits sufficient flexibility to readily permit inward deflection of the stiffening element ends 46, 48 toward one another, yet substantially prevents expansion or extension of the ends 46, 48 away from one another when the tensioning member 34 is in the taut state.

Returning to FIG. 1, the fabric sheath 36 is preferably formed about both of the stiffening element 32 and the tensioning member 34. In some embodiments, the fabric sheath 36 comprises a knitted polyester fabric (e.g., Dacron™), although woven, non-woven (e.g., spun-bond, melt-blown, staple fiber matrix, etc.) or braided fabrics are also contemplated, as well as sheaths formed of harvested biological tissue (e.g., pericardial tissue). The fabric sheath 36 may optionally be provided with any of various biocompatible coatings.

Figure 2:
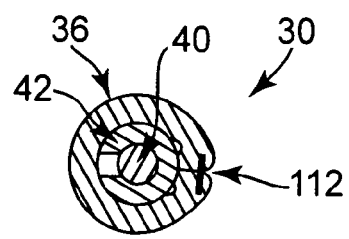
FIG. 2 is a cross-sectional view along the lines 2-2 of FIG. 1.
Figure 9:
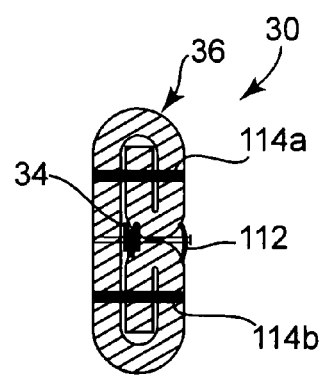
FIG. 9 is a cross-sectional view of the annuloplasty ring of FIG. 1 along the lines 9-9.

The fabric sheath 36 is preferably marked to indicate placement or location of the eyelets 50, 52 otherwise encompassed by the sheath 36 (the second eyelet 52 being referenced generally in FIG. 1). For example, the sheath 36 can be marked to include eyelet placement by a suture 110 of contrasting color to the fabric sheath 36. The suture can form an "X" in the fabric overlying the eyelet 50 and/or 52. Alternatively, the sheath 36 can be marked by any biocompatible marking that indicates the position of the respective eyelet 50 or 52. In some embodiments, a longitudinal seam 112 (identified in FIG. 2 otherwise showing the sheath 36 about the stiffening element 32) is formed along the sheath 36 and is oriented toward an underside of the annuloplasty ring 30 in use so that the seam 112 lies against valve tissue and out of the blood flow path upon implant. The longitudinal seam 112 is continued along the region of the sheath 36 otherwise encompassing the tensioning member 34 as best shown in FIG. 9. In this regard, the sheath 36 can be formed as a continuous structure about an entirety of the stiffening element 32 and the tensioning member 34. In other embodiments, however, the sheath 36 can consist of two or more sections, at least one of which is applied over the stiffening element 32 and another of which is applied over the tensioning member 34. Regardless, and as best shown in FIG. 9, in some embodiments the sheath 36 is folded onto itself in a region of the tensioning member 34 and is retained in a relatively flat shape via, for example, one or more running stitches 114a, 114b. With this configuration, then, the annuloplasty ring 30 is characterized as being flattened in the region of the tensioning member 34, with a maximum thickness or profile of the annuloplasty ring 30 being defined along the stiffening element 32 (FIG. 2). In addition, and as shown in FIG. 1, in some embodiments, the annuloplasty ring 30 further includes stitching 116 and 118 formed through the sheath 36 in a region of the tensioning member 34 directly adjacent the respective ends 46 and 48 of the stiffening element 32. With this configuration, the stitching 116, 118 prevents fraying of the sheath 36 in the event the sheath 36 is accidentally cut by the surgeon. It also prevents perforation of the stiffener eyelet through the fabric if cut by a stitching end near a possible cut point.

In some embodiments, construction of the annuloplasty ring 30 as described above preferably provides a low profile attribute. More particularly, the annuloplasty ring 30 has, in some embodiments, a maximum cross-sectional thickness of no greater than about 3 mm, more preferably no greater than about 2.7 mm, even more preferably no greater than about 2.5 mm. In yet other embodiments, the annuloplasty ring 30 for use in repairing a mitral valve annulus has a reduced size/ratio to address ischemic and dilated cardiomyopathic pathologies. By way of reference, for mitral valve applications, the annuloplasty ring 30 can be described as having a major axis diameter $D_{maj}$ (e.g., distance between the opposing sides of the annuloplasty ring 30 immediately adjacent the stiffening element ends 46, 48), and a minor axis diameter $D_{min}$ (e.g., distance between a region of the annuloplasty ring 30 along the tensioning member 34 and a region directly opposite the tensioning member 34). With these conventions in mind, in some embodiments, a ratio of the minor axis diameter $D_{min}$/major axis diameter $D_{maj}$ is less than 0.6, and in some embodiments is in the range of 0.4-0.6. By way of comparison, currently available annuloplasty rings and rigid annuloplasty bands exhibit a minor axis diameter $D_{min}$/major axis diameter $D_{maj}$ ratio (sometimes referred to as the A/P ratio) of more than 0.6, for example in the range of 0.618-0.711. Alternatively, however, the annuloplasty ring 30 in accordance with principles of the present invention can assume a wide variety of other sizes.

As previously described, the tensioning member 34 is substantially non-extensible in the taut state. Once again, reference to a "taut state" is indicative of the tensioning member 34 being placed under tension via forces applied to the annuloplasty ring 30 that otherwise impart a laterally-expansive load onto the stiffening element ends 46, 48. Even if the tensioning member 34 is in a taut state, it will still be flexible as permitted by the ends 46 and 48 moving toward one another. In some embodiments, "substantially non-extensible" is in reference to the tensioning member 34 experiencing only a slight longitudinal elongation in the presence of a tensile load when the tensioning member 34 is otherwise in the taut state. To this end, the substantially non-extensible characteristic of the tensioning member 34 is evidenced upon by subjecting the annuloplasty ring 30 to a pulling test as described below.

For example, an appropriate tensile load-applying system, such as a model 1011 Instron test machine (Calibration No. 52147) can be used to subject the annuloplasty ring 30 to a tensile load across the tensioning member 34. With this approach, pull test fixtures are clamped in the jaws of the test machine, followed by mounting of the annuloplasty ring 30 to the fixtures. The annuloplasty ring 30 is then subject to a pulling force imparted to the annuloplasty ring 30 at opposite sides of the tensioning member 34 (i.e., adjacent the first and second ends 46, 48 of the stiffening element 32, such that the tensile force is effectively applied along the major axis diameter $D_{maj}$). Thus, the applied tensile load tends to pull the first and second ends 46, 48 away from one another. The substantially non-extensible characteristic of the tensioning member 34 is characterized in terms of the amount of displacement experienced by the annuloplasty ring 30 when subjected to the tensile load described above. With this in mind, in some embodiments, the substantially non-extensible characteristic of the tensioning member 34 is exhibited by the annuloplasty ring 30 experiencing a lateral displacement (or increase in lateral spacing $L_N$ between the first and second ends 46, 48 of the stiffening element 32) of not more than 0.2 inch in the presence of a tensile load (as described above) of one pound. In other embodiments, the substantially non-extensible feature is characterized by a lateral displacement in the presence of a one pound pull test tensile load of not more than 0.15 inch. In other embodiments, the substantially non-extensible nature of the tensioning member 34 is characterized by the annuloplasty ring 30 experiencing a displacement of not more than 0.2 inch in the presence of a pull test load of two pounds. Along these same lines, the substantially non-extensible characteristic is highlighted by removing or severing the tensioning member 34 and then re-subjecting the modified annuloplasty ring 30 to the pull test described above. Under these circumstances, the annuloplasty ring 30 in accordance with principles of the present invention exhibits the lateral displacement of not more than 0.2 inch in response to the one pound pull test load with the tensioning member 34 in tact (and in the taut state), and a lateral displacement of greater than 0.3 inch in response to the one pound pull test load with the tensioning member 34 removed or disconnected.

It is to be understood, however, that while particular embodiments of the invention have been illustrated for use in typical valve repair procedures, various modifications, including modifications to shape, and arrangement of parts, and the degree of permitted extensibility, can be made as may be desirable for varying applications as may relate to valve sizes or later developed techniques.

Figure 10:
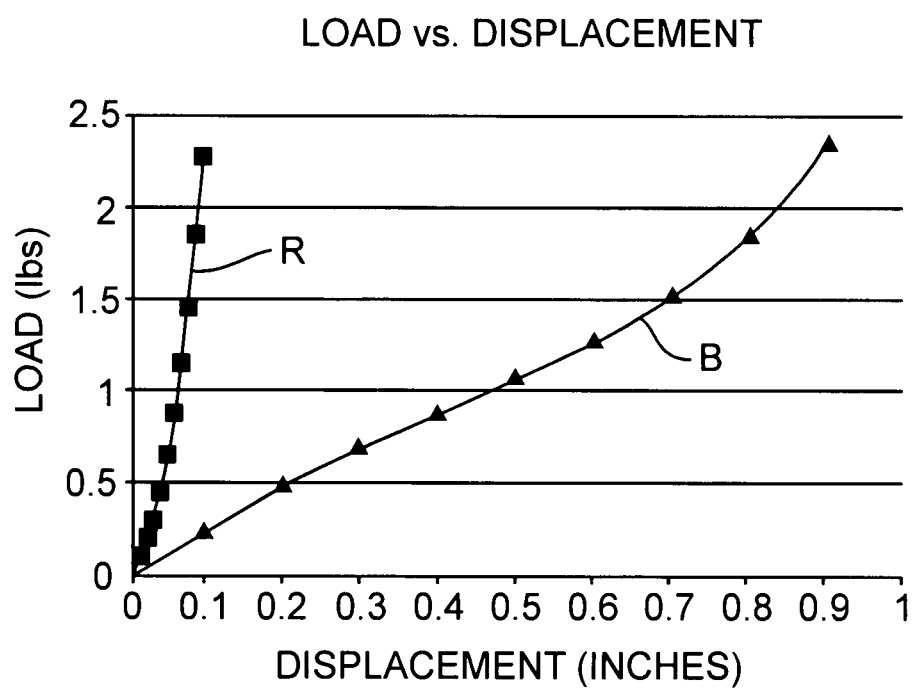
FIG. 10 is a graph illustrating results of pull testing performed on one embodiment annuloplasty ring in accordance with principles of the present invention and on an available annuloplasty band.

Commensurate with the above description of the pull test, sample annuloplasty rings (having a major axis diameter of 24 mm) were constructed in accordance with principles of the present invention (i.e., a stiffening element consisting of a MP35N wire overmolded with an LSR silicone material; a tensioning member consisting of a 4-0 suture looped between opposed ends of the stiffening element to form seven segment links; and a knitted polyester fabric sheath) and subjected to the pull test. Several annuloplasty bands (having a major axis diameter of 26 mm) available under the tradename Future Band™ (from Medtronic, Inc. of Fridley, Minn.), otherwise consisting of a similar stiffening element (i.e., MP35N wire overmolded with LSR silicon material) and sheath, but not including a tensioning member interconnecting the stiffening element ends, were also subjected to the same pull test. FIG. 10 is a plot diagram illustrating the results of these pull tests. The load versus displacement data for annuloplasty ring (i.e., including the tensioning member) is indicated at "R" in FIG. 10, whereas the data for the annuloplasty band (i.e., not including the tensioning member) is indicated at "B". As shown, presence of the tensioning member (R) provided a marked resistance to lateral displacement as compared to the annuloplasty band (B). It should be noted that the example annuloplasty rings are described for purposes of comparison only; the scope of the present invention is in no way limited to the examples.

Figure 11:
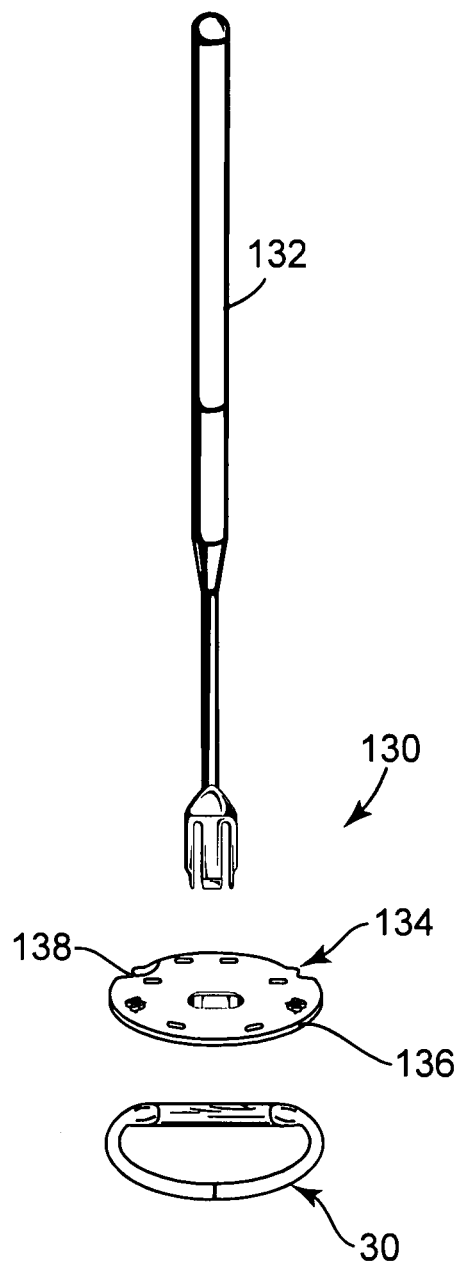
FIG. 11 is an exploded perspective view of annuloplasty ring of FIG. 1 in combination with a holder in accordance with the principles of the present invention.

One embodiment of a holder for use with the annuloplasty ring 30 is illustrated in FIG. 11, and designated in its entirety by the reference numeral 130. The holder 130 includes an elongated handle 132 and a ring-retaining plate 134 selectively mounted on the handle 132. The ring-retaining plate 134 is adapted to retain the annuloplasty ring 30 during implantation of the annuloplasty ring 30. Thus, in accordance with embodiments illustrated in the figures in which the annuloplasty ring 30 is shaped for mitral valve repair, a general perimeter shape of a ring-retaining plate 134 corresponds generally with a shape of a mitral valve annulus (not shown). Alternatively, of course, a perimeter shape of the ring-retaining plate 134 can vary from that shown, and can instead correspond with a shape of an alternatively configured annuloplasty ring 30 (e.g., a tricuspid valve annuloplasty ring).

With the one embodiment shown, however, the ring-retaining plate 134 generally defines a first portion 136 and a second portion 138 each defining a perimeter shape adapted to one or both of generally match a perimeter shape of the annuloplasty ring 30 and/or force the annuloplasty ring 30, or a segment thereof, to a desired shape.

Figure 12A:
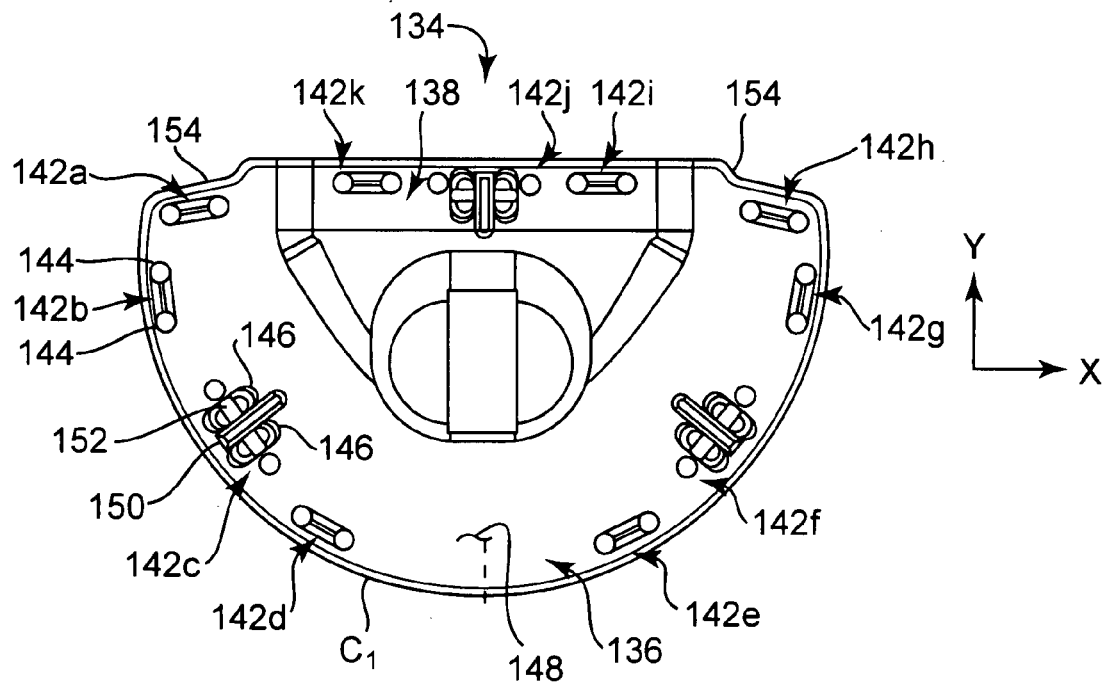
FIG. 12A is a top view of a ring-retaining plate portion of the holder of FIG. 11.
Figure 12B:
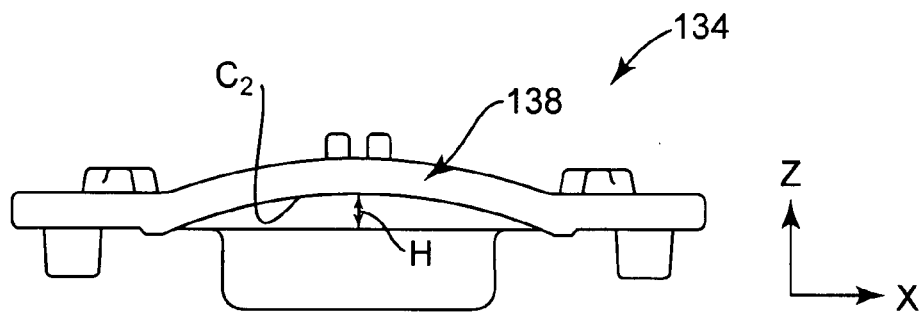
FIG. 12B is an end view of the ring-retaining plate of FIG. 12A.

More particularly, and with reference to FIGS. 12A and 12B, a perimeter of the first portion 136 preferably defines a curvature C, in a first plane (i.e., the plane of the page of FIG. 12A), for example, the X-Y plane. The curvature C, approximates a curvature defined by the stiffening element 32 (FIG. 1), such that when the annuloplasty ring 30 (FIG. 1) is assembled to the ring-retaining plate 134 (as described below), the curvature C, of the first portion 136 matches or mimics the predefined curvature of the annuloplasty ring 30 along a region of the stiffening element 32. Since preferably the tensioning member 34 of the annuloplasty ring 30 is flexible, it may be shaped by the ring-retaining plate 134 for purposes of implantation. As a point of reference, in some embodiments where the stiffening element 32 has a saddle shape, the ring-retaining plate 134 can provide a similar shape (i.e., the first portion 136 can further define a change in shape or curvature in the Z direction). As a further point of reference, where the annuloplasty ring 30 is for use in repairing a mitral valve, the stiffening element 32, and thus the first portion 136, corresponds with a posterior aspect of the mitral valve annulus.

Regardless of an exact shape of the perimeter of the first portion 136, in one embodiment, a perimeter of the second portion 138 can also define a curvature $C_2$ in a second plane as best shown in FIG. 12B. The curvature $C_2$ of the second portion 138 perimeter is defined as a change in the Z direction (or X-Z plane of the page of FIG. 12B), and serves to shape the corresponding region of the annuloplasty ring 30 (FIG. 1) to a saddle shape upon final assembly. In one embodiment, the second curvature $C_2$ defines a change in height H in the range of 0.4-0.1 inch, although other dimensions are equally acceptable. Regardless, the second curvature $C_2$ is in a plane differing from a plane of the first curvature $C_1$ (FIG. 12A), and in some embodiments is in a plane substantially perpendicular to a plane of the first curvature $C_1$.

In some embodiments and with specific reference to FIG. 12A, the ring-retaining plate 134 is adapted to receive one or more drawstrings or sutures 140 (see, e.g., FIG. 13) that is or are otherwise employed to secure the annuloplasty ring 30 (FIG. 1) to the ring-retaining plate 134. For example, the ring-retaining plate 134 forms a plurality of spaced passage pairs 142a-142k. Each passage pair 142a-142k includes two holes 144 (best illustrated in FIG. 12A for the passage pair 142b) extending transversely through the ring-retaining plate 134. Each of the holes 144 is adapted to allow passage of the drawstring suture 140. Further, the holes 144 comprising any one of the passage pairs 142a-142k are separated by a section of the ring-retaining plate 134. That is to say, each of the passage pairs 142a-142k includes two distinct holes 144 and is not a continuous slot. With this configuration, the drawstring suture 140 can be threaded around, and thus engaged by, the ring-retaining plate 134 as shown. In some embodiments, the passage pairs 142c, 142f, and 142j further include two fingers 146 projecting from an upper surface 148 of the ring-retaining plate 134. The fingers 146 are positioned between the respective holes 144, and are spaced from one another to define a slot 150. Further, each of the fingers 146 forms a channel 152 for receiving the drawstring suture 140. With this configuration, and as described in greater detail below, the fingers 146 raise the drawstring suture 140 away from the upper surface 148 and provide a space (i.e., the slot 150) for severing the drawstring suture(s) 140. Finally, in some embodiments, the ring-retaining plate 134 forms cut-outs 154 for reasons described below.

Figure 13:
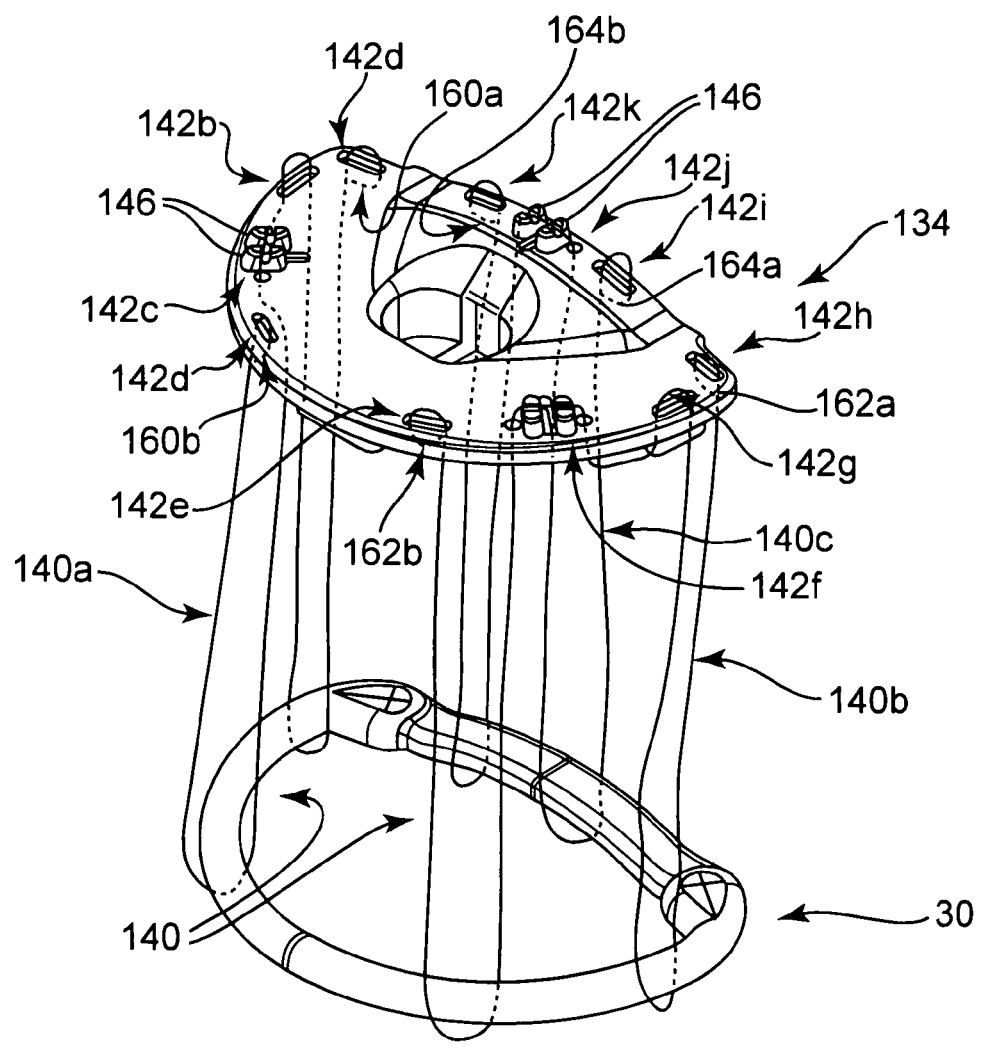
FIG. 13 is a perspective, exploded view illustrating assembly of the annuloplasty ring of FIG. 1 to the ring-retaining plate of FIGS. 12A and 12B.

With the above description in mind, the annuloplasty ring 30 is secured to the ring-retaining plate 134 by threading one or more of the drawstring suture(s) 140 through the passage pairs 142a-142k as shown in FIG. 13. In one embodiment, a first drawstring suture 140a is extended from the first passage pair 142a (and forming a knot 160a) downwardly and around the annuloplasty ring 30; upwardly from the annuloplasty ring 30 to the second passage pair 142b and then below the ring-retaining plate 134; upwardly to the third passage pair 142c and around the respective fingers 146; downwardly from the ring-retaining plate 134 and around the annuloplasty ring 30; upwardly from the annuloplasty ring 30 and around the fourth passage pair 142d; finally, terminating in a knot 160b. A second drawstring suture 140b is similarly employed to connect the annuloplasty ring 30 to the ring-retaining plate 134 via the fifth-eighth passage pairs 142e-142h (including formation of knots 162a and 162b). Alternatively, a single drawstring suture 140 can be employed to connect the annuloplasty ring 30 to the ring-retaining plate 134 via the first-eighth passage pairs 142a-142h. Regardless, a third drawstring suture 140c can be provided that extends from the ninth passage pair 142i (and forming a knot 164a) downwardly and around the annuloplasty ring 30; upwardly from the annuloplasty ring 30 to the tenth passage pair 142j and around the respective fingers 146; downwardly from the tenth passage pair 142j and around the annuloplasty ring 30; upwardly from the annuloplasty ring 30 and around the eleventh passage pair 142k; finally terminating at a knot 164b. In other embodiments, a single drawstring suture 140 is employed; and in other embodiments, four or more drawstring sutures 140 are provided. Notably, directional terminology such as "upper," "upwardly," "downwardly," "below," etc., are used for purposes of illustration and with reference to the orientation of FIG. 13. The annuloplasty ring 30 and/or the ring-retaining plate 134 can be positioned in a wide variety of other orientations, such that the directional terminology is in no way limiting.

The above-described mounting technique is but one available technique for securing the annuloplasty ring 30 to the ring-retaining plate 134. In alternative embodiments, the drawstring suture(s) 140 is or are sewn to the annuloplasty ring 30 at discrete and spaced apart locations.

Final assembly of the annuloplasty ring 30 to the ring-retaining plate 134 is illustrated in FIGS. 14A-14C. As depicted by the top view of FIG. 14A, the cut-outs 154 provide clearance about the eyelets 50, 52 (hidden in FIG. 14A, but readily identified by the markings 110 on the sheath 36). Further, the drawstring suture(s) 140 is easily severed via the slots 150 provided by the fingers 146. With respect to the bottom view of FIG. 14B, the annuloplasty ring 30 is effectively mounted to a bottom surface 170 of the ring-retaining plate 134. In one embodiment, the bottom surface 170 further forms spaced tabs 172, 174, and 176 that serve to generally support a shape of the annuloplasty ring 30 upon final assembly to the ring-retaining plate 134.

The tabs 172-176 preferably do not form grooves or other sidewall curvatures for receiving the annuloplasty ring 30 and in some embodiments do not follow a circumferential profile of annuloplasty ring 30. Instead, the tabs 172-176 extend, in one embodiment, in a perpendicular fashion relative to a plane of the bottom surface 170 and are tangent to the annuloplasty ring's 30 profile at three points, thereby promoting ease of manufacture of the ring-retaining plate 134 as well as ease of removal of the annuloplasty ring 30 from the plate 134. The tabs 172-176 provide points of contact with the annuloplasty ring 30, and there can be more or fewer of these tabs 172-176, also with different configurations, in other embodiments.

As previously described, alternative configurations/techniques can be employed for selectively mounting the annuloplasty ring 30 to the ring-receiving plate 134. To this end, the ring-retaining plate 134 can be configured to maintain the annuloplasty ring 30 in a manner that does not require the drawstring suture(s) 140. For example, in one alternative embodiment, the tabs 172-176 are modified to each add a rib (or radially outward projection) spaced from the bottom surface 170. Taken in combination, these ribs provide a radius of curvature that is slightly greater than that defined by the annuloplasty ring 30. With this configuration, assembly of the annuloplasty ring 30 to the ring-retaining plate 134 entails first expanding the annuloplasty ring 30 (i.e., forcing the ends 46, 48 away from one another) so that the annuloplasty ring 30 can be placed over the ribs. Once properly positioned, the expansion formed on the annuloplasty ring 30 can be released, allowing the annuloplasty ring 30 to contact the tabs 172-176 such that the annuloplasty ring 30 is retained by the tabs 172-176 between the ribs and the bottom surface 170. Following implant to a valve annulus, the annuloplasty ring 30 can be released from the ring-retaining plate 134 by simply pulling the ring-retaining plate 134 away from the annuloplasty ring 30 via maneuvering.

With respect to the end view of FIG. 14C, the drawstring suture 140c forces the corresponding region of the annuloplasty ring 30 to at least generally correspond to the curvature $C_2$ defined by the second portion 138 of the ring-retaining plate 134. In some embodiments, the corresponding region of the annuloplasty ring 30 is defined along the tensioning member 34 (hidden in FIG. 14C, but shown in FIG. 1); thus, where the tensioning member 34 is flexible, the tensioning member 34 and thus the annuloplasty ring 30, will readily conform to the shape defined by the ring-retaining plate 134. Upon final assembly, the annuloplasty ring 30 is found to have a saddle shape along at least the second portion 138 of the ring-retaining plate 134. Once released from the ring-retaining plate 134 (e.g., severing of the third drawstring suture 140c), the tensioning member 34, and thus the annuloplasty ring 30 in the corresponding region thereof, is readily transitionable from the shape imparted by the ring-retaining plate 134. In other embodiments described below, the tensioning member 34 can include a slightly more rigid construction; under these circumstances, the ring-retaining plate 134, and in particular the second portion 138, will assume a shape corresponding with the shape defined by this more rigid construction such that upon release from the ring-retaining plate 134, the tensioning member 34, and thus the annuloplasty ring 30, may maintain the predefined shape.

An additional component useful as part of an implantation procedure for the annuloplasty ring 30 is a sizer device. The device includes a handle and a sizer body. The sizer body is configured to be selectively assembled to the handle, and defines a perimeter corresponding generally with a shape of the annuloplasty ring 30 (FIG. 1).

A plurality of differently sized, but similarly shaped, sizers are preferably provided to a surgeon as such may be different for the valve of the subject procedure, such as the mitral or tricuspid valves. Each of the different sized sizers would preferably correspond with an available annuloplasty ring 30. During use, then, a surgeon would evaluate the valve annulus to be repaired with several differently sized sizers (on an individual basis). Once the sizer most closely corresponding with the valve anatomy is identified, the annuloplasty ring 30 corresponding with the sizer would then be selected for the patient.

Implantation of the annuloplasty ring 30, for example, using the holder 130 (FIG. 11) in accordance with principles of the present invention to repair various heart valves, and in particular, the atrio-ventricular valves, is akin in some embodiments to the examples set forth in U.S. Pat. No. 6,786,924, the teachings of which are incorporated herein by reference. In general terms, the sizer, and in particular, the sizer body is employed to evaluate the valve annulus in question, and based upon this evaluation, used to select an appropriately-sized annuloplasty ring 30 (FIG. 1).

Figure 15:
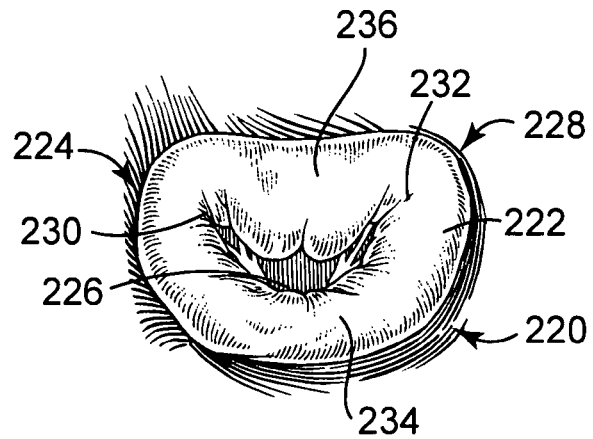
FIG. 15 is a top view of a mitral valve.
Figure 16:
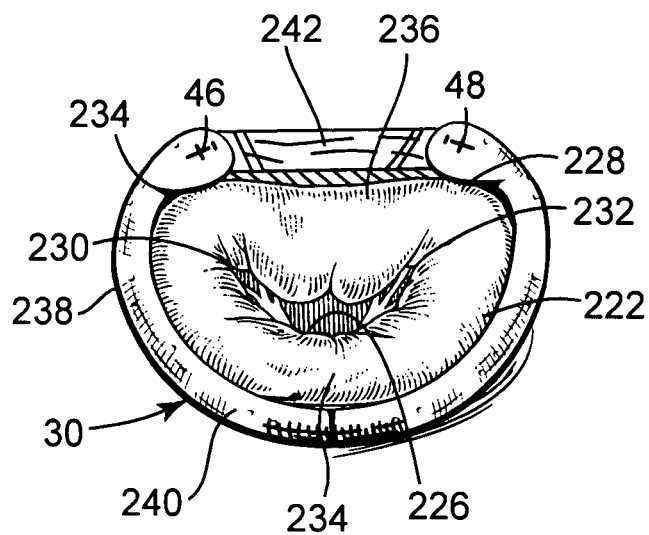
FIG. 16 is a top view of an annuloplasty ring in accordance with principles of the present invention mounted to the valve annulus of the mitral valve of FIG. 15.

With the desired annuloplasty ring size in mind, the selected annuloplasty ring 30 is then assembled to the holder 130 as shown in FIG. 11. The annuloplasty ring 30 is then directed to the implant site via maneuvering of the holder 130 and implanting sutures are employed to connect the annuloplasty ring 30 to the valve annulus. By way of reference, FIG. 15 illustrates portions of the anatomy of a mitral valve 220, including a valve annulus 222, an anterior lateral trigone 224, a posterior leaflet 226, a postero-medial trigone 228, an inferior commissure 230, and a superior commissure 232. With these conventions in mind, the mitral valve annulus 222 defines or is defined by a posterior aspect 234 and an anterior aspect 236. FIG. 16 illustrates the annuloplasty ring 30 secured or implanted to the mitral valve annulus 222 via implanting sutures 238.

In light of the implantation orientation relative to the valve annulus 222 of FIG. 16, the annuloplasty ring 30 can be described as including or defining a posterior segment 240 and an anterior segment 242. The posterior segment 240 corresponds with the posterior aspect 234 of the mitral valve annulus 222, and is defined along a region of the stiffening element 32 (hidden in the view of FIG. 16, but shown in FIG. 1). The anterior segment 242 corresponds with the anterior aspect 236 of the mitral valve annulus 222, and is defined along a region of the tensioning member 34 (hidden in FIG. 16, but shown in FIG. 1). As such, upon final implant, the posterior segment 240 of the annuloplasty ring 30, and in particular the stiffening element 32 associated therewith, serves to rigidly or semi-rigidly re-model a shape of the posterior aspect 234 to a desired extent. Conversely, the anterior segment 242 flexes or moves with natural movement of the anterior aspect 236, and impedes overt dilatation of the anterior aspect 236 by limiting separation of the stiffening element ends 46, 48 (referenced generally in FIG. 18). In other embodiments, the anterior segment 242 of the annuloplasty ring 30 can have a slightly more rigid configuration (e.g., the tensioning member 34 can include a relatively thin wire that, while being more flexible than the stiffening element 32, has a predetermined shape that otherwise serves to assist in reforming the anterior aspect 236 to a certain extent). With this alternative configuration, the anterior segment 242 is still capable of moving with natural movement of the anterior aspect 236 and impedes overt dilatation of the annuloplasty ring 30, and in particular the stiffening element 32, when in a taut state.

Annuloplasty rings in accordance with principles of the present invention provide a marked improvement over previous designs. Unlike conventional annuloplasty rings, the annuloplasty ring in accordance with principles of the present invention facilitates natural movement of a corresponding aspect of the valve annulus being repaired while providing sufficient resistance to overt dilatation of the repaired valve.

Although the present invention has been described with reference to preferred embodiments, workers skilled in the art will recognize that changes can be made in form and detail without departing from the spirit and scope of the present invention.

What is claimed is:

1. An annuloplasty ring for repairing an atrio-ventricular valve having a valve annulus, the annuloplasty ring comprising:
   a sheath;
   an arcuate stiffening element within the sheath, the stiffening element defining discrete first and second ends that are turned back toward one another and that are separated by a lateral spacing, wherein the stiffening element, in a natural state, provides a first segment of the prosthesis that defines a majority of an arcuate annular shape of the annuloplasty prosthesis; and
   a tensioning member extending between the stiffening element ends;
   wherein the tensioning member is characterized as being more flexible than the stiffening element and is configured as a linear element in a taut state between the turned-back first and second ends of the stiffening element in its natural shape in which the tensioning member is substantially non-extensible so as to limit expansion of the lateral spacing between the first and second ends when the annuloplasty ring is subjected to an expansive movement external force, while permitting the first and second ends to flex toward one another when subjected to a compressive movement external force.

2. The annuloplasty ring of claim 1, wherein upon final assembly, the ring is configured such that the tensioning member naturally assumes the taut state.

3. The annuloplasty ring of claim 1, wherein the tensioning member is transitionable from the taut state to a flexed state in which the tensioning member defines a saddle shape.

4. The annuloplasty ring of claim 1, wherein the tensioning member is configured such that in the taut state, the lateral spacing between the first and second ends increases by no more than 0.2 inch when the annuloplasty ring is subjected to a lateral tensile load of one pound.

5. The annuloplasty ring of claim 4, wherein the annuloplasty ring is characterized by exhibiting an increase in the lateral spacing of more than 0.3 inch when subjected to the lateral tensioning load of one pound in the absence of the tensioning member.

6. The annuloplasty ring of claim 1, wherein the tensioning member includes a suture connected to the first and second ends of the stiffening element.

7. The annuloplasty ring of claim 6, wherein the suture is looped between the first and second ends of the stiffening element to define a plurality of segment links.

8. The annuloplasty ring of claim 7, wherein the suture is assembled to the stiffening element to form at least one self-tightening knot.

9. The annuloplasty ring of claim 7, wherein a first end of the suture is secured to the first end of the stiffening element by a first knot and a second end of the suture is secured to the second end of the stiffening element by a second knot.

10. The annuloplasty ring of claim 6, wherein the tensioning member includes a plurality of sutures.

11. The annuloplasty ring of claim 6, wherein the stiffening element includes a wire forming an eyelet at each of the first and second ends, and further wherein the suture is connected to each of the eyelets.

12. The annuloplasty ring of claim 1, wherein the tensioning member is entirely disposed within the sheath.

13. The annuloplasty ring of claim 12, wherein the sheath defines a first portion encompassing the stiffening element and a second portion extending between the first and second ends to encompass a majority of the tensioning member, the second portion having a first section adjacent the first end, and a second section adjacent the second end, the annuloplasty ring further comprising:
   first stitching through the first section of the sheath; and
   second stitching through the second section of the sheath;
   wherein the stitching is configured to limit fraying of the sheath.

14. The annuloplasty ring of claim 1, wherein the stiffening element has a saddle shape.

15. The annuloplasty ring of claim 1, wherein the annuloplasty ring defines a major axis diameter adjacent the stiffening element ends, and a minor axis diameter between the tensioning member and the stiffening element at a point opposite the tensioning member, and further wherein a ratio of the minor axis diameter/major axis diameter is not greater than 0.6.

16. The annuloplasty ring of claim 15, wherein the ratio is in the range of 0.4-0.6.

17. The annuloplasty ring of claim 1, wherein the tensioning member includes a flexible wire imparting an out-of-plane curvature to the tensioning member in a natural state relative to a major plane defined by the stiffening element.

18. A combination annuloplasty ring and holder for use by a surgeon in conjunction with annuloplasty surgery performed on a patient's heart valve defining a valve annulus, the combination comprising:
   an annuloplasty ring including:
   a sheath,
   an arcuate stiffening element within the sheath, the stiffening element defining discrete first and second ends that are turned back toward one another and that are separated by a lateral spacing, wherein the stiffening element, in a natural state, provides a first segment of the prosthesis that defines a majority of an arcuate annular shape of the annuloplasty prosthesis,
   a tensioning member extending between the stiffening element ends,
   wherein the tensioning member is characterized as being more flexible than the stiffening element and is configured as a linear element in a taut state between the turned-back first and second ends of the stiffening element in its natural shape in which the tensioning member is substantially non-extensible so as to limit expansion of the lateral spacing when the annuloplasty ring is subjected to an expansive movement external force, while permitting the first and second ends to flex toward one another when subjected to a compressive movement external force, and
   a holder selectively maintaining the annuloplasty ring, the holder including a ring-retaining plate forming a first curvature in a first plane corresponding generally to a curvature of the stiffening element, and a second curvature in a second plane differing from the first plane for retaining the tensioning member in a curved orientation.

19. The combination of claim 18, wherein the second plane is generally perpendicular to the first plane.

20. The combination of claim 18, wherein the tensioning member is configured to conform to the second curvature.

21. The combination of claim 20, wherein the tensioning member is configured to be transitionable from the second curvature upon being released from the ring-retaining plate.

22. An annuloplasty ring for implantation to a mitral valve annulus, the annuloplasty ring comprising:
   a sheath,
   an arcuate stiffening element within the sheath, the stiffening element defining discrete first and second ends that are turned back toward one another and that are separated by a lateral spacing, wherein the stiffening element, in a natural state, provides a first segment of the prosthesis that defines a majority of an arcuate annular shape of the annuloplasty prosthesis; and
   a tensioning member extending between the stiffening element ends, the tensioning member being characterized as being more flexible than the stiffening element and is configured as a linear element in a taut state between the turned-back first and second ends of the stiffening element in its natural shape in which the tensioning member is substantially non-extensible so as to limit expansion of the lateral spacing when the annuloplasty ring is subjected to an expansive movement external force, while permitting the first and second ends to flex toward one another when subjected to a compressive movement external force;
   wherein the annuloplasty ring defines:
   an anterior segment along a region corresponding with the tensioning member, the anterior segment adapted to be implanted at an anterior aspect of the mitral valve annulus,
   a posterior segment along a region corresponding with the stiffening element, the posterior segment adapted to be implanted at a posterior aspect of the mitral valve annulus;
   and further wherein the stiffening element is adapted to remodel the mitral valve annulus and the tensioning member is configured to conform to a natural anatomy of the anterior aspect of the mitral valve annulus.

23. The annuloplasty ring of claim 22, wherein the tensioning member is configured to provide a taut state in which the tensioning member is substantially non-extensible and impedes expansion of the lateral spacing between the first and second ends of the stiffening element when the annuloplasty ring is subjected to an external force.

24. The annuloplasty ring of claim 22, wherein the tensioning member is configured to move with movement of the anterior aspect of the mitral valve annulus.

25. The annuloplasty ring of claim 22, wherein the stiffening element has a shape generally conforming with a natural systolic shape of the posterior aspect of the mitral valve annulus.

26. The annuloplasty ring of claim 22, wherein the stiffening element has a saddle shape.

* * * * *